United States Patent [19]

Yabe et al.

[11] Patent Number: 5,538,496
[45] Date of Patent: Jul. 23, 1996

[54] ENDOSCOPE COVER TYPE ENDOSCOPE

[75] Inventors: Hisao Yabe; Akira Suzuki; Minoru Yamazaki; Hideo Ito, all of Hachioji; Yoshihiro Iida, Tama; Yoshio Tashiro, Hino; Osamu Tamada, Hachioji, all of Japan

[73] Assignee: Olympus Optical Co., Ltd., Tokyo, Japan

[21] Appl. No.: 34,674

[22] Filed: Mar. 19, 1993

[30] Foreign Application Priority Data

Feb. 1, 1993 [JP] Japan ................. 5-002270 U
Feb. 1, 1993 [JP] Japan ................. 5-002271 U
Feb. 1, 1993 [JP] Japan ................. 5-014957

[51] Int. Cl.$^6$ ................. A61B 1/00; A61B 1/008
[52] U.S. Cl. ................. 600/141; 600/142; 600/121; 600/131
[58] Field of Search ................. 128/4; 600/141, 600/142, 139, 146, 149, 143, 140, 121, 123

[56] References Cited

U.S. PATENT DOCUMENTS

| Re. 34,110 | 9/1992 | Opie . | |
|---|---|---|---|
| 3,162,190 | 12/1964 | Del Gizzo . | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,947,827 | 8/1990 | Opie et al. | 128/4 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,271,381 | 12/1993 | Ailinger et al. | 128/4 |

FOREIGN PATENT DOCUMENTS

| 0184778 | 6/1986 | European Pat. Off. . |
|---|---|---|
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-29634 | 2/1991 | Japan . |
| 3-29635 | 2/1991 | Japan . |
| 3-37029 | 2/1991 | Japan . |
| 3-13105 | 2/1991 | Japan . |
| 3-37030 | 2/1991 | Japan . |
| 3-221024 | 9/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| 3-101901 | 10/1991 | Japan . |
| 3-101902 | 10/1991 | Japan . |
| 4-325138 | 11/1992 | Japan . |

*Primary Examiner*—Stephen R. Crow
*Assistant Examiner*—Beverly M. Flanagan
*Attorney, Agent, or Firm*—Armstrong, Westerman, Hattori, McLeland & Naughton

[57] ABSTRACT

A covering endoscope having a curving portion composed of a plurality of curving pieces and an observation optical system and an endoscope cover having an inserting path for inserting the endoscope and a contained unit provided along the inserting path. A side of the curving pieces facing the contained unit is formed of flat surfaces and a coupling portion coupling adjacent ones of the curving pieces are provided in a position near the flat surfaces from a center of the endoscope.

1 Claim, 24 Drawing Sheets

FIG. 24(a)
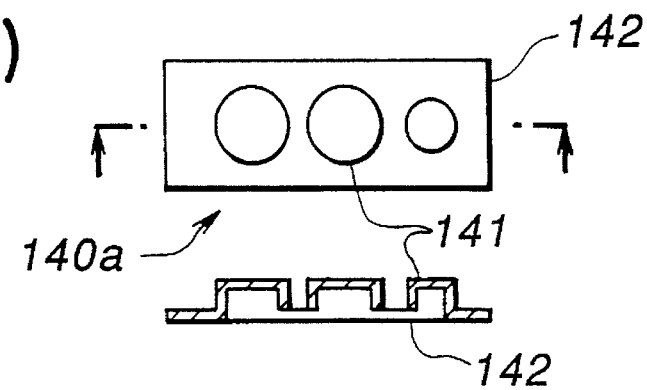
FIG. 24(b)
FIG. 25(a)
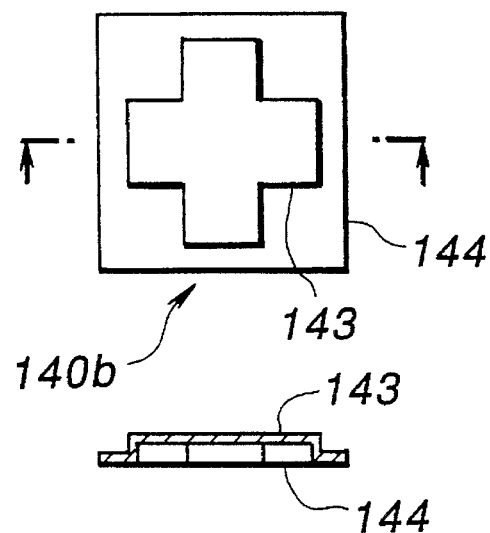
FIG. 25(b)
FIG. 26(a)
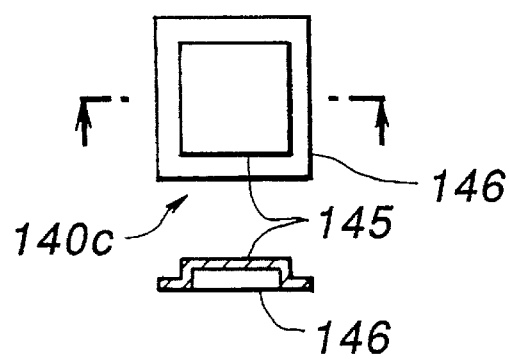
FIG. 26(b)

FIG. 27(a)
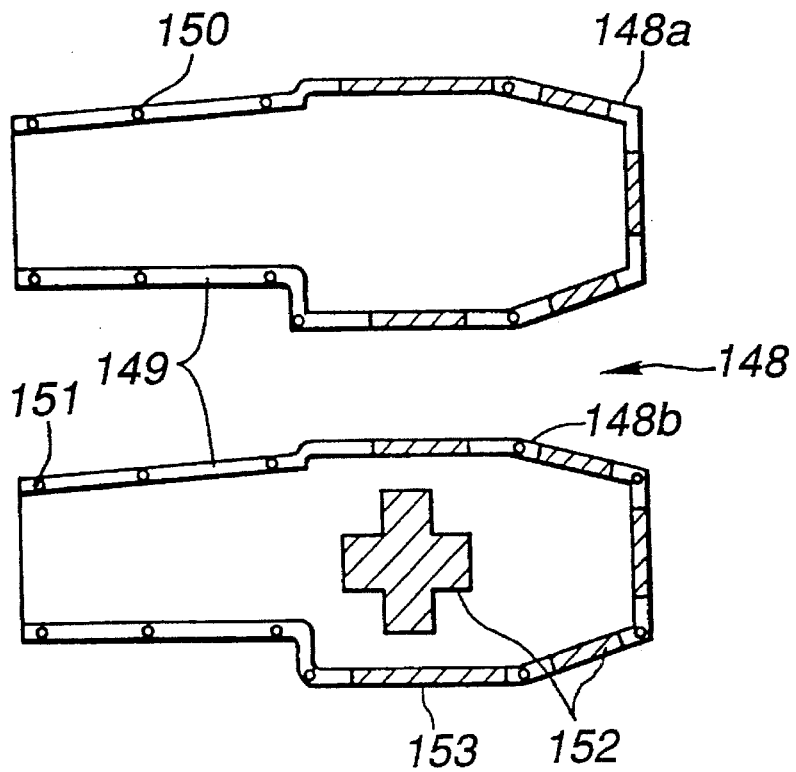
FIG. 27(b)
FIG. 28(a)
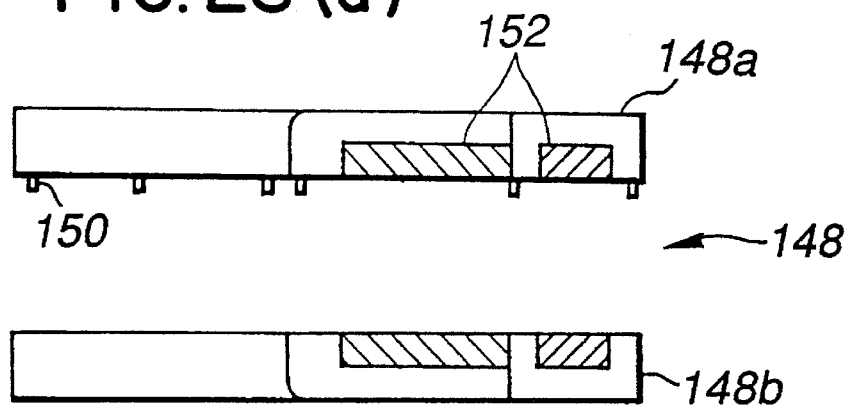
FIG. 28(b)

ENDOSCOPE COVER TYPE ENDOSCOPE

BACKGROUND OF THE INVENTION

1. Field of the Invention

The present invention relates to an endoscope cover type endoscope using an endoscope cover for preventing the contamination of the endoscope.

2. Description of the Related Art

Recently, an endoscope for performing a diagnosis and treatment by inserting a slender inserting portion into a coelom is widely used. In a test performed by using an endoscope, a clean endoscope having been sufficiently rinsed and sterilized prior to the test must be used. Therefore, an endoscope contaminated by being used in the coelom of a patient is rinsed and sterilized by various methods before it is used to a next patient. However, it takes a very long time to completely and sufficiently rinse the endoscope.

To overcome this drawback, Japanese Examined Patent Publication No. Hei 2-54734, U.S. Pat. No. 3,162,190 disclose a disposable type endoscope cover type endoscope used in place of a repeatedly-usable type endoscope. These proposals intend to prevent the contamination of the endoscope by covering the endoscope with an endoscope cover. More specifically, the endoscope cover type endoscope according to these proposals is composed of an endoscope cover and an endoscope covering endoscope (hereinafter, referred to as a covering type endoscope), and the inserting portion of the covering type endoscope can be covered with the endoscope cover. Contamination of the covering type endoscope is prevented by inserting the covering type endoscope into the coelom of a patient while it is covered with the endoscope cover. Note, after the covering type endoscope is used, the disposable endoscope cover is removed and disposed of.

The inserting portion of the covering type endoscope includes, for example, a photographing system, observing optical system and light guide fiber. On the other hand, since a forceps channel, air and water feed pipes may be contaminated by body fluids and further are difficult to be rinsed and sterilized because they have a slender shape, these channels are integrally mounted to the endoscope cover and disposed of together with it. That is, the endoscope cover is provided with a channel for treatment tools and pipes having an opening at the opposite ends thereof such as air and water feed pipes. Note, an endoscope cover provided with a channel of endoscope covers may be referred to as an endoscope cover with a channel. Further, a covering type endoscope to be inserted into the endoscope cover with a channel may be referred to as an endoscope covering endoscope with a channel.

As described above, the rinsing and sterilization of the covering type endoscope can be made unnecessary by disposing an endoscope cover with a channel used to each patient, and thus this is very sanitary. Since the covering type endoscope need not be rinsed and sterilized, a test effected by using an endoscope can be continuously performed to a plurality of patients.

Incidentally, a repeatedly-usable type endoscope which is not covered with an endoscope cover (hereinafter, referred to as an endoscope without a cover) includes an indicator for indicating an inserting length at an inserting portion. This indication can be used as a yardstick for confirming an observing portion during a test and is also used when a portion changed to a morbid state is recorded.

However, in a conventional endoscope cover type endoscope, even if an indicator for indicating an inserting length is provided to the inserting portion of a covering type endoscope, the inserting portion cannot be visually confirmed because it is covered with the endoscope cover, and thus this indication cannot be used. Therefore, in the conventional endoscope cover type endoscope, the inserted length of the endoscope cannot be confirmed during a test, which is an obstruction for a test and a record of a portion changed to a morbid state.

Incidentally, recently, an ultrasonic endoscope for obtaining an ultrasonic cross sectional image by inserting an ultrasonic probe into a coelom such as a blood pipe is used for various diagnoses. An ultrasonic oscillator serving as an ultrasonic wave transmitter/receiver is provided at the extreme end of the ultrasonic prove inserted into the lumen to generate an ultrasonic wave for diagnosis and to receive an echo from an observing portion.

It is contemplated to use a disposable endoscope cover also for this ultrasonic endoscope. That is, the ultrasonic endoscope is used as a covering type endoscope (hereinafter, referred to as an ultrasonic covering type endoscope). Conventionally, however, an endoscope cover used to insulate the ultrasonic covering type endoscope from the outside is not different from that used for a covering type endoscope, such as an electronic or optical type fiber scope, and does not have a sufficient ultrasonic wave transmittance. Therefore, when the endoscope is covered with an endoscope cover, a drawback arises in that it cannot obtain an ultrasonic image.

In a test effected by using a usual ultrasonic endoscope not using an endoscope cover (with a channel), a deaerated water feed method or balloon method is used, taking into consideration that an ultrasonic wave is greatly attenuated in air. In the deaerated water feed method, a test is effected in the state that deaerated water is fed to a lumen, and in the balloon method, a test is effected in the state that deaerated water is fed to a balloon provided with an ultrasonic endoscope. Both methods remove an air layer causing the attenuation of an ultrasonic wave by filling the portion between a lumen wall and an ultrasonic wave transmitting/receiving unit with deaerated water, and a good ultrasonic image is obtained by effecting a test in this state.

When, however, the covering type ultrasonic endoscope is covered with the endoscope cover, an air layer is formed between the endoscope cover and the covering type ultrasonic endoscope, and thus a problem arises in that a good ultrasonic image cannot be obtained.

Incidentally, the inserting portion of the covering type endoscope has one end capable of being curved so that any desired direction can be observed and diagnosed, and a switch for the curving operation is disposed on the operating unit. Further, the operating unit is also provided with an air/water feed switch for controlling the feed of air and water through an air/feed pipe and also with a sucking switch for controlling the sucking operation for sucking bodily fluids and the like. Further, a function switch for photographing and the like is also disposed. In addition, a universal cord is connected to the operating unit on the hand side thereof and a slender inserting portion is connected to the extreme end side thereof.

Conventionally, there is a case in which the portion of an endoscope cover for covering the operating unit (hereinafter, referred to as an operating unit cover) is composed of a sheet member. Nevertheless, as described above, since many switches are disposed on the operating unit and further the universal cord and inserting portion are connected thereto, the operating unit is formed to have a very complicated configuration. Therefore, the method of covering the operating unit with the sheet-shaped operation unit cover makes a mounting job very time-consuming, and further when it is not correctly mounted, the operation unit may not be entirely covered.

Thus, a hard operating unit cover molded of hard plastic is proposed. The hard operating unit cover has an inner surface shaped substantially contrary to the outer surface of the operating unit and a structure to be divided into two parts. The operating portion cover can be mounted in such a manner that a pair of the operating portion covers are mated to each other with the operating unit held therebetween. That is, the workability of a mounting job is improved by using the hard operating unit cover and this operating unit cover is sufficient to entirely cover the operating unit. When, however, the operating unit is covered with the hard operating unit cover, a drawback arises in that a large force is required to operate the switches disposed on the surface of the operating unit and the operation thereof is difficult.

Incidentally, the curving portion at the extreme end of the inserting portion of the cover type endoscope is composed of a plurality of curving pieces connected to each other. A wire is connected to the curving piece at the most extreme end and pulled by rotating a curving knob disposed on the operating unit to curve the curving portion.

A curved knob cover for covering the curving knob to prevent the contamination thereof must be able to be rotated. Therefore, the curving knob cover has a complicated structure and a drawback arises in that the rotation of the curving knob is prevented by the curving knob cover depending upon the structure thereof.

Further, the application of the endoscope is not limited to observation and diagnosis. For example, gas may be removed from an intestine by using an endoscope without a cover. That is, the inserting portion of an endoscope without a cover used for testing a colon is covered with a tube such as a sliding tube and the gas in the intestine is removed through a cavity formed by the difference of the inside diameters between the inserting portion and the tube.

In this case, however, since the tube must be previously mounted prior to a test, a job for mounting it is time-consuming and further a drawback arises in that since the insertion of the endoscope without a cover into the intestine is prevented by the tube.

By the way, since the inserting portion of the covering type endoscope has a slender shape, a job for mounting an endoscope cover is relatively difficult. To cope with this problem, there is employed a method of inserting the cover type endoscope into the endoscope cover while the portion of the endoscope cover with which the inserting portion is covered (hereinafter, referred to as an inserting portion cover) is expanded by being fed with air. More specifically, an expansion pump is used to feed air to the inserting portion cover through a tube. On the other hand, air is also fed to the observation window deposed at the extreme end of the endoscope cover type endoscope.

As described above, two kinds of pumps are used in a conventional endoscope cover type endoscope and thus a drawback also arises in that the size and cost of the endoscope apparatus are increased.

Incidentally, the operating unit of the covering type endoscope is connected to a light source through a universal cord and connector. Then, an illuminating light is supplied from the light source to the covering type endoscope through a light guide fiber inserted into the universal cord.

Incidentally, although the universal cord is covered with the universal cord cover of the endoscope cover, the connector portion is sometimes not covered. As a result, a drawback arises in that when the universal cord is mounted to and dismounted from the light source, the connector is contaminated. Further, even if the connector portion is covered, a job for mounting it is relatively difficult because the connector is connected to the universal cord.

Further, the conventional endoscope cover type endoscope also has a drawback in that the inserting portion thereof is insufficiently curved. FIG. 52 is an explanatory diagram showing the state that the inserting portion of an endoscope is mounted to the inserting portion cover of an endoscope cover with a channel, wherein: FIG. 52(*a*) is a cross sectional view thereof cut in a radius direction; and FIG. 52(*b*) shows a side cross sectional view thereof cut in a longitudinal direction.

The inserting portion cover 301 of the endoscope cover with a channel includes an air feed tube 302, water feed tube 303 and a suction tube 304 on the upper surface side thereof. Hereinafter, these units contained in the upper surface side of the inserting portion cover 301 are also referred to as a contained unit 310. Further, the inserting portion cover 301 includes an endoscope inserting channel 305 for inserting the inserting portion of the covering type endoscope on the lower surface side thereof. As described above, since these tubes 302, 303, 304 are disposed, the inserting portion 306 of the covering type endoscope is not disposed at the center of the inserting portion cover 301 but disposed eccentrically on the lower surface side of thereof, as shown in FIG. 52.

Note, the outer circumference of the inserting portion cover 301 is covered with a soft inserting portion cover casing 307. Further, a cover extreme end portion 309 for covering the inserting portion extreme end 308 of the covering type endoscope is formed at the extreme end of the inserting portion cover 301.

Incidentally, the extreme end of the inserting portion 306 of the covering type endoscope can be curved so that an observation and diagnosis can be effected in any arbitrary direction. A curving angle of the extreme end when the inserting portion 306 is covered with the inserting portion cover 301 is smaller than a curving angle when the inserting portion 306 is independently curved due to the resistance against the curving of the inserting portion cover 301.

FIG. 53 is an explanatory diagram explaining a curving angle of the inserting portion 306 to which the inserting portion cover 301 is mounted.

The inserting portion 306 includes a soft portion 311, curving portion 312 capable of being curved and hard extreme end portion 308 from the hand side to the extreme end thereof. It is assumed now that the curving portion 312 has a curving radius R1. In this case, as shown in FIG. 53, the inserting portion 306 is curved about 90°. Further, it is assume that the curving portion 312 has a curving radius R2 smaller than the curving radius R1. In this case, the inserting portion 306 has a curving angle of about 180°. As described above, when a curving length is the same, a curving angle is larger as a curving radius is smaller.

Now, it is assumed that the inserting portion 306 is curved in the direction toward the contained unit 310. In this case, as shown in FIG. 52, when it is assumed that the contained unit 310 has a curving radius b, the inserting portion 306 has a curving radius d larger than b. Further, when the inserting portion 306 is curved to a lower surface side and it is assumed that the contained unit 310 and inserting portion 306 have a curving radius a, c, respectively, a>c is established.

The curving radius b of the contained unit 310 in an upper surface direction must be smaller than the curving radius a thereof in a lower surface direction in order that the curving radius c of the inserting portion 306 in the lower surface direction coincides with the curving radius d thereof in the upper surface direction. When this is achieved, however, a curving resistance caused by the contained unit 310 is increased. Therefore, a large force is required to achieve a sufficient curving. On the other hand, when the inserting portion 306 is curved to the lower surface side, the inserting portion cover casing 307 must has a curving radius smaller than that of the inserting portion 306, and it is sufficient that the contained unit 310 having the relatively large curving resistance is curved by a curving radius large than that of the inserting portion 306, and even if the inserting portion 306 is covered with the inserting portion cover 301, the effect thereof to a curving operation is relatively small. After all, a problem arises in that the inserting portion 306 is difficult to be curved to the upper surface side, in particular, in the direction toward the contained unit 310 and thus a small curving radius cannot be obtained.

For example, a curving angle of the inserting portion 306 as a single body is set to 10° in each direction and the inserting portion 306 is covered with the inserting portion cover 301, a curving angle of 170° can be obtained in all directions except the direction toward the contained unit 310 but only a curving angle of 160° is contained in the direction toward the contained unit 310.

Incidentally, the inserting portion cover includes a forceps port communicating with a treatment tool channel. The forceps port is used together with accessories such as a T-shaped tube, thruster, forceps stopper, or the like, or a mouth piece attached thereto, when necessary.

However, the inserting portion cover is sterilized and then disposed of, whereas the accessories attached to the forceps port are repeatedly used. Therefore, a drawback arises in that each time the conventional endoscope covering type endoscope is used, these accessories must be sterilized.

The inserting portion cover of the endoscope cover is formed to have a slender shape and is composed of a cover extreme end portion, flexible cover portion, and endoscope operating unit fixing mouth member disposed from the extreme end thereof. The inserting portion of the covering type endoscope is inserted through the opening of an endoscope inserting channel provided with the endoscope operating unit fixing mouth member and the hand side of the endoscope operating unit fixing mouth member is connected to the extreme end of the operating unit of the covering type endoscope.

The operating unit includes a mounting unit for mounting the universal cord through which the light guide fiber for transmitting an illuminating light, and the like are inserted. The universal cord is inserted from the light source to the operating unit and inserting portion to transmit the illuminating light to the extreme end of the inserting portion. On the other hand, the air feed tube, water feed tube, suction tube and the like are inserted into the interior of the inserting portion cover from a fluid control unit through the opening on the hand side of the endoscope operating unit fixing mouth member of the inserting portion cover.

These tubes are exposed between the inserting portion cover and the fluid control unit and the setting of these tubes are time-consuming. Further, although it is contemplated that these tubes are used in a state in which they are disposed along the universal cord, since the mounting portion of the universal cord is spaced apart from the opening on the hand side of the endoscope operating unit fixing mouth member, the tubes cannot be easily set. Therefore, a drawback arises in that an operation effected on the operating unit is prevented thereby.

Incidentally, a plurality of types of the covering type endoscopes are available in accordance with the purposes to which they are applied. For example, these endoscopes have an inserting portion with a different diameter and length. On the other hand, a plurality of types of the inserting portion covers are available in correspondence with the diameters and lengths of the inserting portions.

Further, a plurality of types of inserting portion covers are applicable to a kind of the covering type endoscope. For example, a forceps channel shared with a suction tube has a different diameter. Further, many covering type endoscopes applicable to a kind of the inserting portion cover are available. For example, a covering type endoscope employing an electrically curving system, angle knob system is available. In addition, there are a plurality of kinds of the number of pixels used in a photographing device provided in the observing optical system of the covering type endoscope.

An operator selects a desired endoscope cover in correspondence with a selected covering type endoscope and mounts the same. However, there are a great many possible combinations of the covering type endoscopes and endoscope covers and thus there is a great possibility that undesired endoscope cover is mounted by mistake.

SUMMARY OF THE INVENTION

An object of the present invention is to provide an endoscope cover type endoscope by which the inserting length of an inserting portion can be known even in the state in which an endoscope cover is mounted.

Another object of the present invention is to provide an endoscope cover type endoscope by which a good ultrasonic image can be obtained.

Another object of the present invention is to provide an endoscope cover type endoscope in which the switches on an operating unit can be operated well and an operating unit cover can be easily mounted.

Another object of the present invention is to provide an endoscope cover type endoscope in which a gas removing job can be easily effected.

Another object of the present invention is to provide an endoscope cover type endoscope capable of making the size of an apparatus small by providing a shared pump as an expansion pump and air/water feed pump.

Another object of the present invention is to provide an endoscope cover type endoscope by which a universal cord cover and connector can be covered with a simple mounting job.

Another object of the present invention is to provide an endoscope cover type endoscope in which a desired curving angle can be obtained in any desired direction.

Another object of the present invention is to provide an endoscope cover type endoscope in which an assembling job can be improved.

Another object of the present invention is to provide an endoscope cover type endoscope which can be securely used in a sterilized state.

Another object of the present invention is to provide an endoscope cover type endoscope by which tubes can be easily set.

Another object of the present invention is to provide an endoscope cover type endoscope in which a suitable combination of an endoscope cover and covering type endoscope can be easily determined.

An endoscope cover type endoscope according to the present invention comprises an endoscope covering endoscope including an inserting portion on which an indication is displayed and an endoscope cover for covering at least the inserting portion and isolating the same from the outside and including a portion having a transparency enabling at least the indication to be visually conformed from the outside.

Further, an endoscope cover type endoscope according to the present invention comprises an endoscope covering endoscope including an inserting portion provided with an ultrasonic wave transmitting/receiving unit, and an endoscope cover for covering at least the inserting portion and isolating the same from the outside, wherein the portion of the endoscope cover corresponding to the ultrasonic wave transmitting/receiving unit is composed of an ultrasonic wave transmitting material and deaerated water can be fed between the portion and the inserting portion.

Further, an endoscope cover type endoscope according to the present invention comprises an endoscope covering endoscope including an operating unit disposed on the hand side thereof and an operating unit cover for covering the operating unit and isolating the same from the outside and composed of a soft switch cover for covering the switches disposed on the operating unit and a hard cover for covering the portion other than the switches.

Further, an endoscope cover type endoscope according to the present invention comprising an endosocope covering endoscope including an operating unit and a universal cord connected to the hand side of the operating unit for connecting the operating unit to a light source through a connector and an endoscope cover for covering at least the universal cord and isolating the same from the outside and integrally provided with a connector accommodating unit disposed at the end thereof for accommodating the connector.

Further, an endoscope cover type endoscope according to the present invention comprises an endoscope covering endoscope, an endoscope cover for covering the endoscope covering endoscope and an inserting portion as the extreme end portion of the endoscope covering endoscope capable of being curved at an angle larger than a required curving angle in the state that the endoscope cover is mounted.

Further, an endoscope cover type endoscope according to the present invention comprising an inserting portion cover for covering the inserting portion of an endoscope covering endoscope, wherein the inserting portion cover is assembled by a first step for fixing tubes in an endoscope operation unit fixing mouth member, a second step for connecting an inserting portion cover casing to the endoscope operation unit fixing mouth member, and a third step for connecting the tubes and the inserting portion cover casing to a cover extreme end.

BRIEF DESCRIPTION OF THE DRAWINGS

FIG. 1 to FIG. 7 relate to a first embodiment according to the present invention: wherein, FIG. 1 is an overall perspective view of an endoscope apparatus using an endoscope covering type endoscope with a channel;

FIG. 2 is a side cross sectional view showing the state that the inserting portion cover of an endoscope cover with a channel is mounted to the inserting portion of a covering type endoscope;

FIG. 3 is a front view showing the state that the inserting portion cover of an endoscope cover with a channel is mounted to the inserting portion of a covering type endoscope;

FIG. 4 is a front view showing the inserting portion cover of an endoscope cover with a channel;

FIG. 5 is a perspective view showing the extreme end of the inserting portion of a covering type endoscope;

FIG. 6 is a perspective view showing the extreme end and its vicinity of the inserting portion cover of an endoscope cover with a channel;

FIG. 7 is an explanatory diagram showing the cross section of an inserting portion cover in the state that a covering type endoscope is inserted;

FIG. 15 to FIG. 28 relate to a sixth embodiment according to the present invention, wherein:

FIG. 15 is an explanatory diagram showing the vicinity of the operating unit of an endoscope cover type endoscope with a channel;

FIG. 16 is an enlarged diagram showing the portion A in FIG. 15 in enlargement;

FIG. 17 is an overall perspective view of an endoscope apparatus using an endoscope cover type endoscope with a channel;

FIG. 18 is a side cross sectional view showing the state that the inserting portion cover of an endoscope cover with a channel is mounted to the inserting portion of a covering type endoscope;

FIG. 19 is an explanatory diagram showing a covering type endoscope;

FIG. 20 is an explanatory diagram showing the electrically operated curving unit of a covering type endoscope;

FIG. 21 is a circuit block diagram enabling a curving drive;

FIG. 22 is a side view showing the various switches disposed on an inserting unit;

FIG. 23 is a front view of FIG. 22;

FIGS. 24(A) and 24(B) to FIGS. 26(A) and 26(b) are diagrams explaining and showing a switch cover;

FIGS. 27(A), 27(b), and 28(b) are explanatory diagrams showing a hard cover;

FIG. 46 is viewed from the line B—B thereof;

DETAILED DESCRIPTION OF THE PREFERRED EMBODIMENTS

Embodiments according to the present invention will be described below with reference to the drawings.

Figure 1:
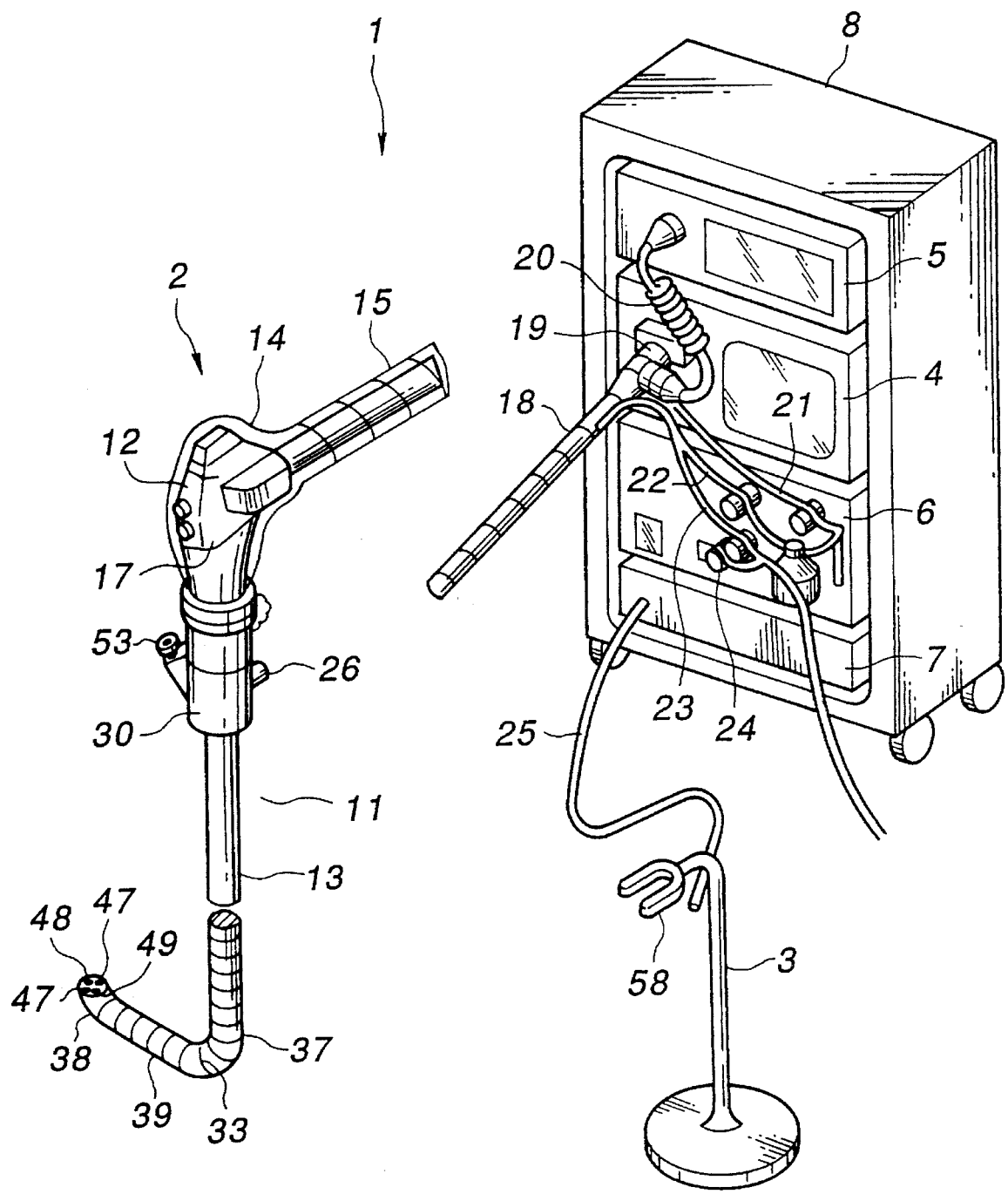
Figure 2:
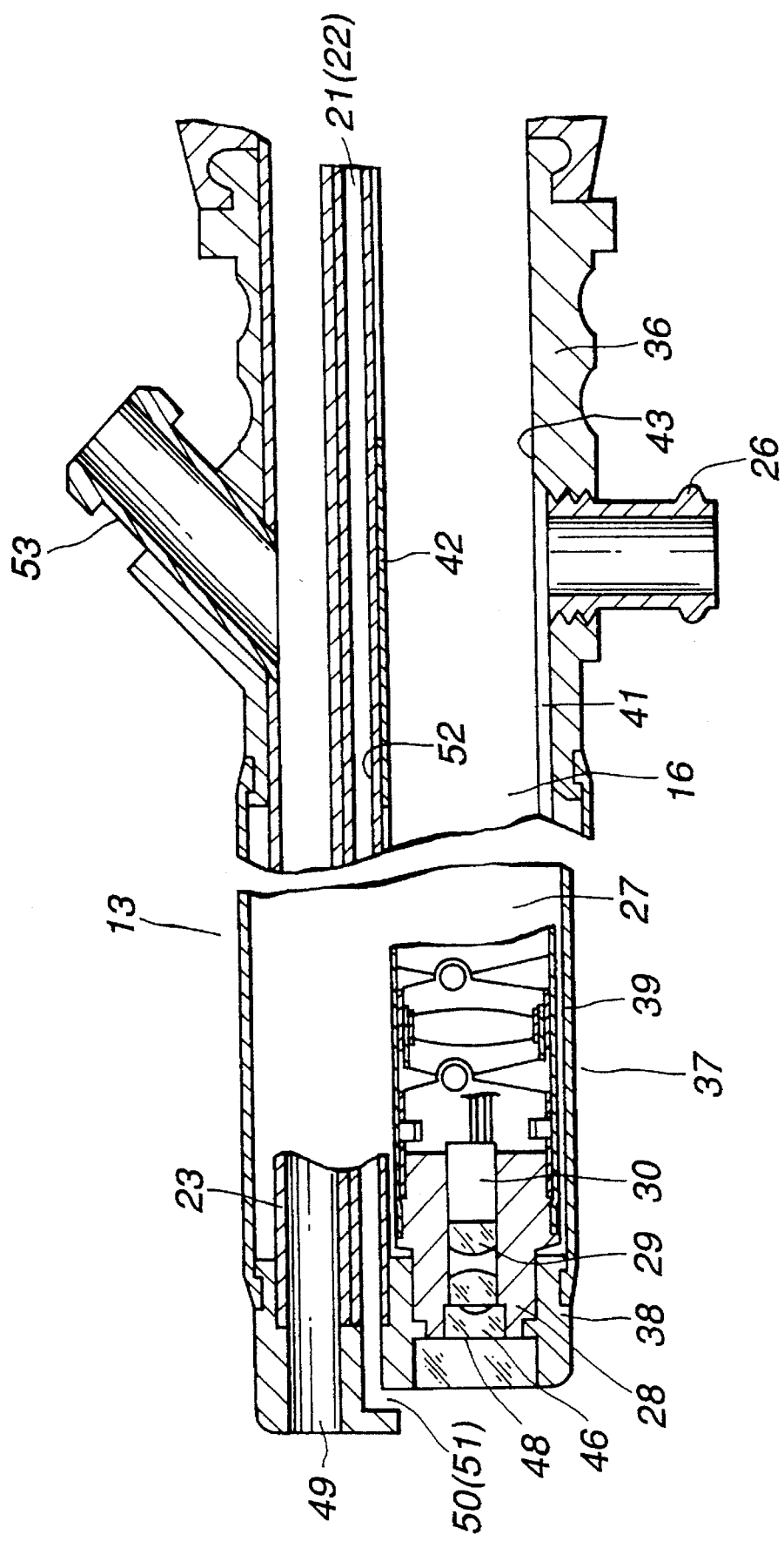
Figure 3:
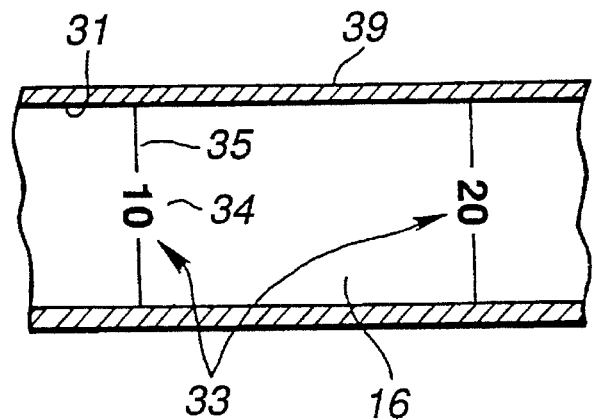
Figure 4:
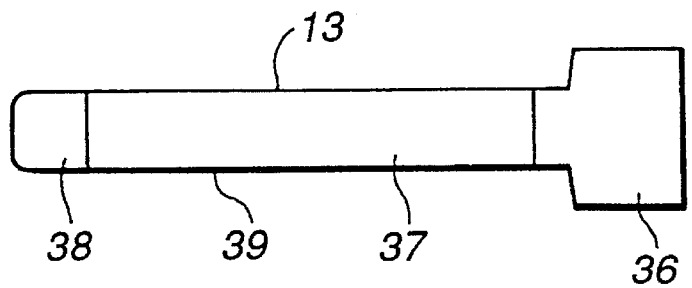
Figure 5:
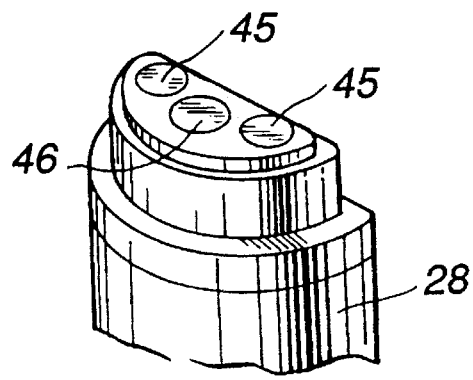
Figure 6:
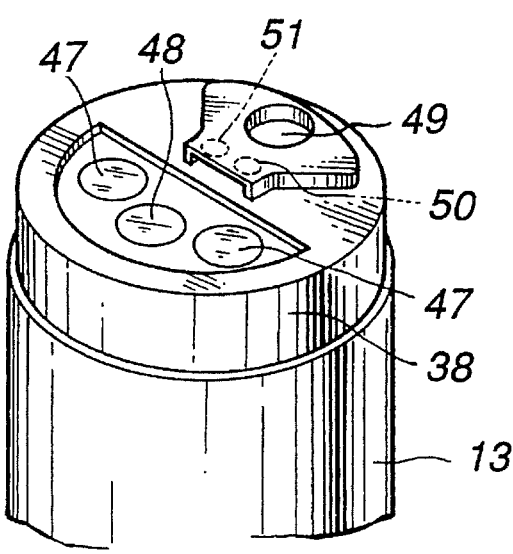
Figure 7:
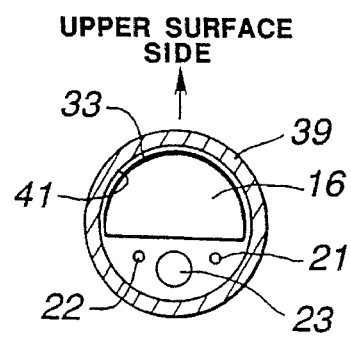

FIG. 1 to FIG. 7 relate to a first embodiment according to the present invention: wherein, FIG. 1 is an overall perspective view of an endoscope apparatus using an endoscope cover type endoscope with a channel; FIG. 2 is a side cross sectional view showing the state that the inserting portion cover of an endoscope cover with a channel is mounted to the inserting portion of a covering type endoscope; FIG. 3 is a front view showing the state that the inserting portion cover of an endoscope cover with a channel is mounted to the inserting portion of a covering type endoscope; FIG. 4 is a front view showing the inserting portion cover of an endoscope cover with a channel; FIG. 5 is a perspective view showing the extreme end of the inserting portion of a covering type endoscope; FIG. 6 is a perspective view showing the extreme end and its vicinity of the inserting portion cover of an endoscope cover with a channel; and FIG. 7 is an explanatory diagram showing the cross-section of an inserting portion cover in a state in which a covering type endoscope is inserted.

An endoscope apparatus 1 shown in FIG. 1 is composed of an endoscope cover type endoscope with a channel 2, cover holder 3, light source 4 as a peripheral unit, video processor 5, fluid control unit 6, endoscope cover expansion unit 7, and a cart 8 in which these peripheral units are accommodated. The endoscope cover type endoscope with a channel 2 is composed of a combination of an endoscope cover with a channel 11 and covering type endoscope 12 and when a test is performed, the covering type endoscope 12 is covered with the endoscope cover with a channel 11. The endoscope cover with a channel 11, which covers the inserting portion 16 and the like of the covering type endoscope 12 so that the endoscope need not be rinsed and sterilized after the test has been completed, is composed of an inserting portion cover 13, operating unit cover 14, and universal cord cover 15.

The light source 4 supplies an illuminating light to the covering type endoscope 12. The covering type endoscope 12 includes an operating unit 17 and the inserting portion 16 (refer to FIG. 2), and a universal cord 18 is extended from the operating unit 17. The universal cord 18 is detachably connected to the light source 4 through a connector 19, and the illuminating light from the light source 4 is supplied to the covering type endoscope 12 by a light guide fiber (not shown) passing through the universal cord 18. Further, a signal line for transmitting an electrical signal from the covering type endoscope 12 is also disposed in the universal cord and connected to the video processor 5 through a signal cord 20 extending from the side of the connector 19. The video processor 5 converts an electric signal from the electronic covering type endoscope 12 to a standard video signal.

The fluid control unit 6 includes a water feed source (not shown) and air feed unit and feeds air and water through an air feed tube 21 and water feed tube 22, respectively, as well as performs suction through a suction tube 23. Note, as described later, the air feed tube 21, water feed tube 22 and suction tube 23 are integrally attached to the endoscope cover with a channel 11. These tubes 21, 22 and 23 are opened and closed by an electromagnetic valve 24.

Further, the endoscope cover expansion unit 7 can be connected to an expansion tube mouth member 26 of the endoscope cover with a channel 11 through an expansion tube 25 and expands the endoscope cover with a channel 11 by feeding air thereinto through the expansion tube 25. This expansion enables the endoscope cover with a channel 11 to be easily mounted to and dismounted from the covering type endoscope 12. The cover holder 3 includes a locking portion 58 so that the inserting portion cover 13 of the endoscope cover 11 can be held by being caught at the locking portion 58. The endoscope cover with a channel can be easily mounted by that it is held by the cover holder 3 and further this is sanitary because the endoscope cover with a channel 11 need not be touched by a human hand when mounted.

FIG. 2 shows the inserting portion 16 of the endoscope cover with a channel 12 covered with the endoscope cover with a channel 11.

The inserting portion 16 of the covering type endoscope 12 includes a soft portion, curving portion 27 capable of being curved and hard extreme end 28 from the hand side to the extreme end thereof. Note, the inserting portion 16 has a cross-section formed to, for example, a semicircular shape to secure a space for the tubes 21 to 23 of the endoscope cover with a channel 11. A illuminating light system (not shown) and observing optical system 29 are disposed at the extreme end 28 of the inserting portion 16. Then, the emitting end of a light fiber guide (not shown) is disposed at the rear end of the illuminating optical system, and an illuminating light supplied from the light source 4 by the light guide fiber passing through the inserting portion 16, operating unit 17 and universal cord 18 illuminates the inside of the lumen. A solid photographing device 30 is disposed at the rear end of the observing optical system 29 to convert a light reflected from an observing portion to an electric signal. The electric signal from the solid photographing device 30 is supplied to the video processor 5 through the aforesaid signal cord 20.

Figure 13:
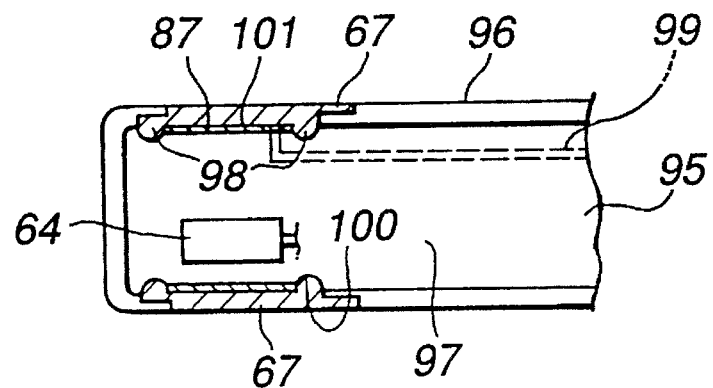
FIG. 13 is an explanatory diagram showing another example to which an ultrasonic covering type endoscope is applied.

The casing 31 of the inserting portion 16 of the covering type endoscope 12 shown in FIG. 13 is composed of a thermoplastic elastomer material such as, for example, black polyurethane, polyester or the like. An indicator 33 for indicating an inserting length is provided on the surface of the casing 31 of the inserting portion 16. The indicator 33 is composed of, for example, a symbol portion 34 where a display such as a numeral indicating an inserting length is shown and a position indicating portion 35 where a display such as a line or the like indicating a position corresponding to the symbol portion 34 is shown. The symbol portion 34 and position indicating portion 35 are formed by printing a thermoplastic elastomer material such as, for example, white polyurethane different from the material of the casing 31 of the inserting portion 16.

On the other hand, the inserting portion cover 13 of the endoscope cover with a channel 11 is used to cover the inserting portion 16 of the covering type endoscope 12, the operating unit cover 14 is used to cover the operating unit 17 of the covering type endoscope, and the universal cord cover 15 is used to cover the universal cord 18. Then, the covering type endoscope 12 is used for a test in a state in which all the covers 13, 14 and 15 are mounted.

The inserting portion cover 13 is formed to have a slender shape and is composed of an endoscope operating unit fixing mouth member 36, flexible cover portion 37 and cover extreme end portion 38 disposed from the hand side, as shown in FIG. 4. The endoscope operating unit fixing mouth member 36 and cover extreme end portion 38 are composed of a hard material. Further, the flexible cover portion 37 between the endoscope operating unit fixing mouth member 36 and the cover extreme end portion is flexible and the surface thereof is covered with an insetting portion cover casing 39.

As shown in FIG. 2, the inserting portion cover 13 includes an endoscope inserting channel 41 through which the inserting portion 16 of the covering type endoscope 12 can be inserted, the air feed tube 21, water feed tube 22 and suction tube 23 in the interior thereof. The endoscope inserting channel 41 is provided with an opening formed of a closing member 42 for closing the portion other than the endoscope inserting channel 41, air feed tube 21, water feed tube 22 and suction tube 23 at the endoscope operating unit fixing mouth member 36. The opening 43 has a diameter substantially the same as that of the inserting portion 16 so that the inserting portion 16 can be inserted into the opening 43 of the endoscope operating unit fixing mouth member 36 in intimate contact therewith. The operating unit 17 of the covering type endoscope 12 and the respective tubes 21, 22, 23 are attached to the endoscope operating unit fixing mouth member 36 and the opening 43 is closed at this time, and thus the inserting portion 16 is mounted in the inserting portion cover 13 in an air tight state.

As shown in FIG. 5, the emitting ends 45 of the illuminating optical system and the incident end 46 of the observing optical system 29 are provided at the extreme end 28 of the inserting portion of the covering type endoscope 12. On the other hand, as shown in FIG. 6, the cover extreme end portion 38 of the inserting portion cover 13 of the endoscope cover with a channel 11 includes transparent illuminating cover windows 47 located at the extreme end of the endoscope inserting channel 41 covering the emitting ends 45 located at the extreme end 28 of the inserting portion and an observation window 48 located at the extreme end of the endoscope inserting channel 41 covering the incident end 46.

The cover extreme end portion 38 of the inserting portion cover 13 projects nearer to the extreme end than the endoscope inserting channel 41, on the side of the air feed tube 21, water feed tube 22 and suction tube 23, and the suction tube 23 communicates with an forceps exit port 49 opened to the extreme end side at the cover extreme end portion 38. An air feed nozzle 50 and water feed nozzle 51, which are bent and opened toward the observing window 48, respectively, are formed at the extreme ends of the air feed tube 21 and water feed tube 22.

The hard cover extreme end portion 38 of the inserting portion cover 13 is connected to the inserting portion cover casing 39 in an air tight state. The extreme end of the inserting portion 16 of the covering type endoscope 12 is isolated from an outside environment by the inserting portion cover casing 39 and the casing 52 of the air feed tube 21 and water feed tube 22. Further, the inserting portion cover casing 39 is connected to the endoscope operating unit fixing mouth member 36 in an air tight state at the hand side thereof and the inserting portion 16 is perfectly isolated from the outside environment at the hand side thereof by the closing member 42 and the inserting portion 16 itself. Note, a forceps inserting port 53 is provided with the endoscope operating unit fixing mouth member 36 and communicated with the suction tube 23.

In this embodiment, the inserting portion cover casing 39 of the endoscope cover with a channel 11 is composed of an elastic material such as, for example, polyurethane, silicon, latex or a polymer material such as teflon and formed to have a tubular shape and thus has a high transparency. Since the inserting portion cover casing 39 has the high transparency, the indicator 33 of the inserting portion 16 can be visually confirmed from the outside of the inserting portion cover casing 39 (hatched portion) when the inserting portion 16 is inserted, as shown in FIG. 3. Note, the inserting portion cover casing 39 has a wall thickness set to a range of, for example, 2 mm or less within which the interior thereof can be visually confirmed so that the transparency thereof can be increased.

In this endoscope cover type endoscope arranged as described above, when the inserting portion 16 of the covering type endoscope 12 is inserted into the inserting portion cover 13, the inserting portion cover casing 39 of the inserting portion cover 13 is located at a position corresponding to the indicator 33 indicated on the casing 31 of the inserting portion 16. Since the inserting portion cover casing 39 has the high transparency, the interior thereof can be visually confirmed from the outside thereof and thus the indicator 33 on the casing 31 of the inserting portion 16 can be confirmed in the state that the endoscope cover with a channel 11 is mounted. With this arrangement, a portion to be observed can be determined while viewing the indicator 33. Further, this indicator can be utilized when a portion changed to a morbid state is recorded and thus the efficiency of a test can be improved.

Note, the endoscope inserting channel 41 of the inserting portion cover 13 is preferably disposed on the upper surface of the endoscope cover type endoscope with a channel 2, as shown in FIG. 7. Further, the indicator 33 on the inserting portion 16 is also disposed on the upper side shown by an arrow.

With this arrangement, the indicator 33 and be visually confirmed from the upper side and thus an inserting length can be easily confirmed while testing.

Figure 8:
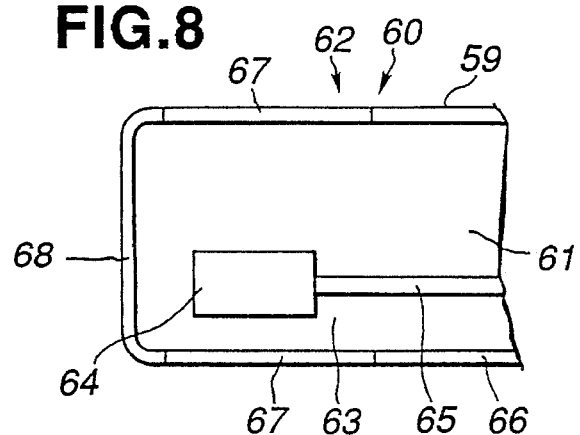
FIG. 8 is an explanatory diagram showing a second embodiment according to the present invention.

FIG. 8 is an explanatory diagram showing a second embodiment according to the present invention. This embodiment shows an example in which the present invention is applied to an ultrasonic covering type endoscope. FIG. 8 shows the extreme end 62 of an endoscope cover type endoscope 60 using an ultrasonic covering type endoscope 61.

The extreme end composing portion 63 of the ultrasonic covering type endoscope 61 includes an ultrasonic observing member 64 composed of an ultrasonic oscillator (not shown), and the ultrasonic observing member 64 is connected to a signal processing unit (not shown) through a cable 65. Further, the extreme end of the inserting portion cover of an endoscope cover 59 for covering the inserting portion of the ultrasonic covering type endoscope 61 is composed of an inserting portion cover casing 66 and cover extreme end portion 68. The cover extreme end portion 68 is connected to the inserting portion cover casing 66 in an air-tight state and thus the contamination of the ultrasonic covering type endoscope 61 is prevented.

In this embodiment, an ultrasonic wave transmitting portion 67 is formed to the portion which confronts the ultrasonic observing member 64 of the cover extreme end portion 68 and inserting portion cover casing 66 in a state in which the inserting portion cover is mounted to the inserting portion of the ultrasonic covering type endoscope 61. The ultrasonic wave transmitting portion 67 is composed of a material excellent in ultrasonic wave transmittance such as, for example, latex, silicon, polyethylene, teflon or the like. Note, the portion of the inserting portion cover casing 66 except the ultrasonic wave transmitting portion 67 is transparent in the same way as the inserting portion cover casing 39 shown in FIG. 1.

In the endoscope cover type endoscope arranged as described above, when the inserting portion of the covering type endoscope 61 is inserted into the inserting portion cover of the endoscope cover 59, the ultrasonic observing member 64 is located in close proximity to the ultrasonic wave transmitting portion 67 at the cover extreme end portion. The ultrasonic wave transmitting portion 67 is excellent in ultrasonic wave transmittance, and thus an ultrasonic oscillation oscillated from the ultrasonic observing member 64 transmits the ultrasonic wave transmitting portion 67. The ultrasonic oscillation having transmitted the ultrasonic wave transmitting portion 67 is reflected from a coelom wall and transmits through the ultrasonic wave transmitting portion 67 again and is read by the ultrasonic observing member 64. The ultrasonic observing member 64 makes the ultrasonic oscillation read thereby to a signal and outputs the same through the cable 65.

As described above, this embodiment enables an ultrasonic diagnosis in a state in which the endoscope cover 59 is mounted, whereby an excellent ultrasonic image can be obtained.

Note, when the ultrasonic observing member 64 confronts only the cover extreme end portion 68 in a state that the inserting portion cover is mounted to the inserting portion of the ultrasonic covering type endoscope 61, the cover extreme end portion 68 as a whole may be composed of a material excellent in ultrasonic wave transmittance. Further, when the ultrasonic observing member 64 confronts only the inserting portion cover casing 66 in a state in which the inserting portion cover is mounted to the inserting portion of the ultrasonic covering type endoscope 61, the inserting portion cover casing 66 may be composed of a material excellent in ultrasonic wave transmittance, in the same way. Further, when the ultrasonic observing member 64 confronts both of the cover extreme end portion 68 and inserting portion cover casing 66 in a state in which the inserting portion cover is mounted to the inserting portion of the ultrasonic covering type endoscope 61, the cover extreme end portion 68 and inserting portion cover casing 66 may be composed of a material excellent in ultrasonic wave transmittance.

FIG. 9 is an explanatory diagram showing a third embodiment according to the present invention.

Figure 9A:
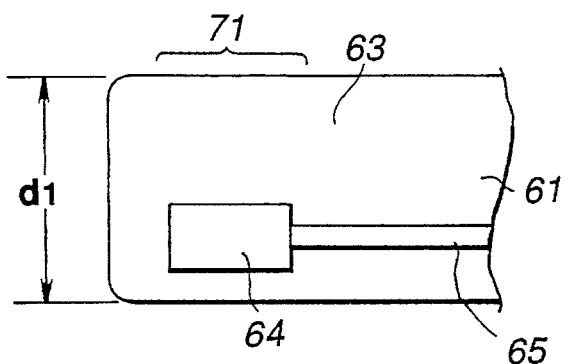
FIGS. 9(A) and 9(B) are explanatory diagrams showing a third embodiment according to the present invention.
Figure 9B:
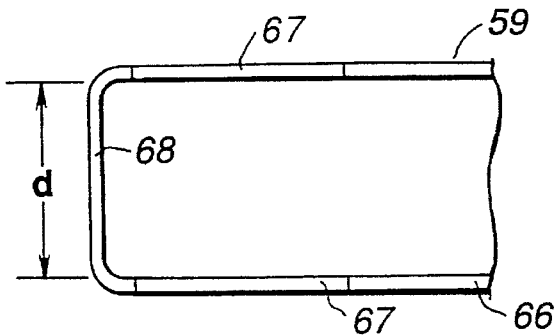

It is necessary to remove an air layer between an ultrasonic endoscope and an observing portion to obtain an excellent ultrasonic image. FIGS. 9(A) and 9(b) show an example achieve by taking this point into consideration. FIG. 9(a) shows an ultrasonic covering type endoscope 61 and FIG. 9(b) shows an endoscope cover 59.

In the ultrasonic covering type endoscope 61 shown in FIG. 9(a), a contained unit 71 as a portion in a radial direction including an ultrasonic observing member 64 of an extreme end composing portion 63 has an outside diameter d1. On the other hand, as shown in FIG. 9(b), in the endoscope cover 59 mounted to the ultrasonic covering type endoscope 61, an ultrasonic wave transmitting portion 67 confronting the ultrasonic observing member 64 has an inside diameter d2 and these diameters are set to d1>d2. Further, the ultrasonic wave transmitting portion 67 is composed of an elastic material.

In the endoscope cover type endoscope arranged as described above, the inserting portion cover of the endoscope cover 59 is inserted into the inserting portion of the ultrasonic covering type endoscope 61 to cause the ultrasonic observing member 64 to confront the ultrasonic wave transmitting portion 67. In the case, although the relationship d1>d2 is established, i.e., the outside diameter of the ultrasonic covering type endoscope 61 is larger than the inside diameter of the endoscope cover 59 at the contained unit 71 and, since the ultrasonic wave transmitting unit 67 is the elastic member, the endoscope cover 59 can be mounted. Then, since d1>d2, the ultrasonic covering type endoscope 61 comes into intimate contact with the endoscope cover 69 at the contained unit 71 without forming any gap therebetween, and thus the air layer is removed.

With this arrangement, the air layer of the ultrasonic observing member 64 in an ultrasonic wave radiating direction can be perfectly removed by employing, for example, a deaerated water feed method, whereby an excellent ultrasonic image can be obtained.

Note, the contained unit 71 of the ultrasonic covering type endoscope 61 sometimes has a cross-sectional shape different from that of the ultrasonic wave transmitting portion 67 of the endoscope cover 59. In this case, when it is assumed that the contained unit 71 has a cross-sectional area A1 and the ultrasonic wave transmitting portion 67 of the endoscope cover 59 has a cross-sectional opening area A2, a relationship satisfying A1>A2 may be established.

Figure 10:
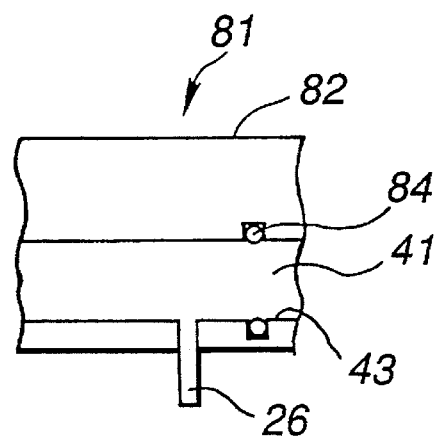
FIGS. 10 and 11 are explanatory diagrams showing a fourth embodiment according to the present invention.
Figure 11:
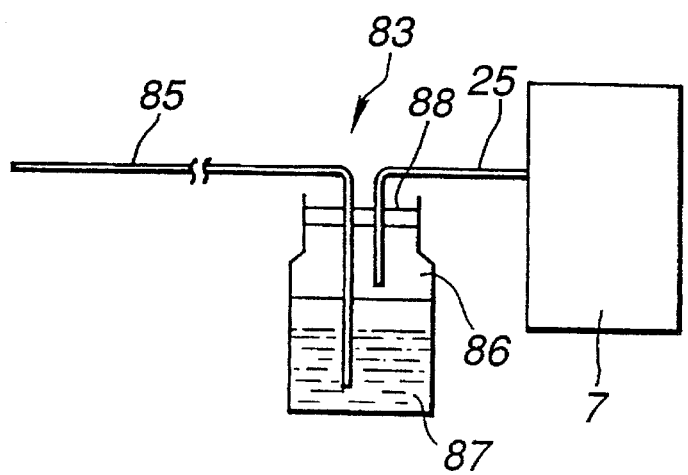

FIGS. 10 and 11 are explanatory diagrams showing a fourth embodiment of the present invention. FIGS. 10 and 11 show another example for removing an air layer between an ultrasonic covering type endoscope and an observing portion, wherein FIG. 10 shows the endoscope operating unit fixing mouth member 82 of an endoscope cover 81; and FIG. 11 shows a deaerated water feed unit 83.

As shown in FIG. 10, the endoscope cover 81 includes an inserting portion cover for covering the inserting portion of the ultrasonic covering type endoscope composed of the endoscope operating unit fixing mouth member 82, flexible cover portion (not shown) on an extreme end side and cover extreme end portion. The inserting portion cover includes an endoscope inserting channel 41 and is communicated with the outside only through the opening 43 of the endoscope inserting channel 41 at the endoscope operating unit fixing mouth member 82.

A water tight member 84 is provided in the inner circumference of the endoscope inserting channel 41 in the vicinity of the opening 43. The water tight member 84 is engaged with the water tight groove provided in the inserting portion of an ultrasonic covering type endoscope (not shown), and thus when the inserting portion of the ultrasonic covering type endoscope is inserted into the endoscope inserting channel 41, they maintain the inserting portion cover in a watertight state. An expansion tube mouth member 26 is disposed on the side of the endoscope inserting channel 41 located nearer to the extreme end side than the watertight member 84 and projects to the outside of the endoscope operating unit fixing mouth member 82. An expansion tube 25 or water feed tube 85 can be attached to the expansion tube mouth member 26.

On the other hand, as shown in FIG. 11, the deaerated water feed unit 83 is composed of an endoscope cover expansion unit 7, the expansion tube 25, a water feed tank 86, tank pressurizing mouth piece 88 and water feed tube 85. The expansion tube 25 connected to the expansion unit 7 can be also attached to the tank pressurizing mouth piece 88 for closing the water feed tank 86 in addition to the expansion tube mouth member 26. Deaerated water 87 is stored in the water feed tank 86. Further, the water feed tank 86 is provided with the water feed tube 85 having an end opened in the vicinity of the bottom in the tank 86 and the other end capable of being connected to the expansion tube mouth member 26 through the tank pressurizing mouth piece 88.

In the endoscope cover type endoscope arranged as described above, when the endoscope cover 81 is mounted, air is fed from the expansion unit 7 to the endoscope cover 81 so that it can be easily mounted. More specifically, first, the expansion tube 25 is connected to the expansion tube mouth member 26 and the ultrasonic covering type endoscope 41 is inserted from the opening 41 while air is fed from the expansion unit 7 to the endoscope inserting channel 41 to expand the same. When the inserting portion has been mounted, the expansion tube 25 is removed from the expansion tube mouth member 26 and attached to the tank pressurizing mouth piece 88. Further, the water feed tube 85 is attached to the expansion tube mouth member 26.

Next, the expansion unit 7 is operated in this state. Then, the water feed tank 86 is expanded by the air fed from the expansion unit 7 through the expansion tube 25 and the deaerated water 87 is also pressurized. With this arrangement, the deaerated water 87 is fed to the endoscope inserting channel 41 through the water feed tube 85 and expansion tube mouth member 26 and then to the gap between the endoscope cover 81 and the ultrasonic covering type endoscope. In this case, since the watertight member 84 is provided, the deaerated water does not leak to the outside from the opening 41.

The deaerated water 87 is sealed in the gap between the endoscope cover 81 and the ultrasonic covering type endoscope, and thus the air layer around the ultrasonic observing member is removed. An excellent ultrasonic image can be obtained by employing the deaerated water feed method also in this case.

Figure 12:
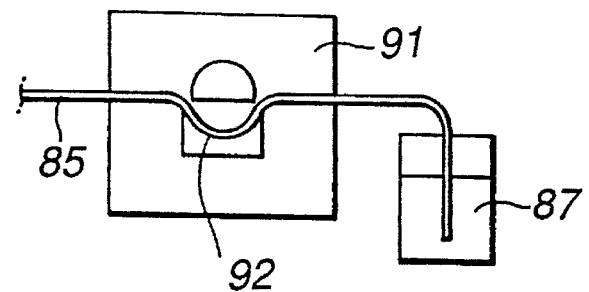
FIG. 12 is an explanatory diagram showing another example of a deaerated water feed unit of FIG. 11.

Note, a roller pump 91 shown in FIG. 12 may be used to feed the deaerated water. The roller pump 91 feeds the deaerated water 87 from the other end of a tube 92 having an end opened in the deaerated water 87 in the tank. Since the other end of the tube 92 is connected to the water feed tube 85, when the roller pump 91 is operated, the deaerated water can be fed to the endoscope cover 81 through the expansion tube mouth member 26.

FIG. 13 is an explanatory diagram showing a fifth embodiment according to the present invention. FIG. 13 shows an example in which deaerated water is fed only to the vicinity of an ultrasonic wave transmitting portion 67, and an ultrasonic covering type endoscope 95 is inserted into an endoscope cover 96.

The extreme end composing portion 97 of the ultrasonic covering type endoscope 95 is provided with a ultrasonic observing member 64 for transmitting an ultrasonic wave in a circumferential direction and receiving the same. When the ultrasonic covering type endoscope 95 is mounted, the ultrasonic wave transmitting portion 67 (the portion hatched in a right direction) is formed to the portion of the endoscope cover 96 confronting the ultrasonic observing member 64, and sealing packings 98 project from the opposite ends on the inner circumference side of the ultrasonic wave transmitting portion 67. A deaerated water feed tube 99 is integrally provided with the endoscope cover 96. An end of the deaerated water feed tube 99 has an opening on the inner circumference of the ultrasonic wave transmitting portion 67 between a pair of the sealing packings 98 and the other end thereof is connected to a deaerated water feed port disposed in the vicinity of an operating unit side (not shown).

On the other hand, a pair of water tight grooves 100 are formed at locations on the outer circumference of the extreme end composing portion 97 of the ultrasonic covering type endoscope 95 in confrontation with the sealing packings 98 and each of them has a shape contrary to the shape of the sealing packings 98. Note, the gap between the ultrasonic covering type endoscope 95 and the endoscope cover 96 located between the pair of sealing packings 98 (the portion hatched in a left direction) is referred to as a deaerated water covering portion 101.

In the endoscope cover type endoscope arranged as described above, when the ultrasonic covering type endoscope 95 is inserted into the endoscope cover 96, the sealing packings 98 are engaged with the watertight grooves 100 at the two locations so that the deaerated water covering portion 101 is sealed. When the deaerated water is fed from a deaerated water feed port in this state, the deaerated water 87 is fed to the deaerated water covering portion 101 through the deaerated water feed tube 99.

With this arrangement, the air layer between the ultrasonic covering type endoscope 95 and the endoscope cover 96 is removed in the circumferential direction of the ultrasonic observing member 64, and thus an excellent ultrasonic image can be obtained by employing the deaerated water feed method.

Figure 14A:
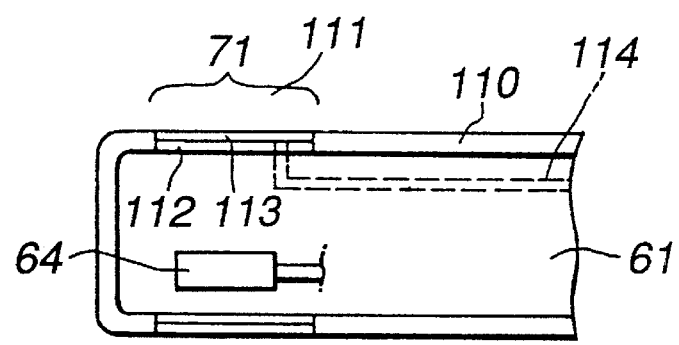
FIGS. 14(A) and 14(b) are explanatory diagrams showing another example to which an ultrasonic covering type endoscope is applied.
Figure 14B:
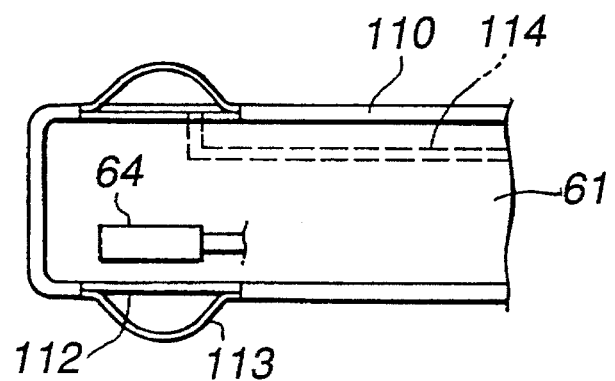

Further, FIGS. 14(A) and 14(b) show an example by which even an air layer outside an endoscope cover can be also removed by employing a balloon method.

An ultrasonic covering type endoscope 61 is arranged in the same way as that shown in FIG. 9. As shown in FIG. 14, an endoscope cover 110 is arranged such that a portion thereof confronting an ultrasonic observing member 64 is provided with a balloon portion 111 composed of two layers. The inside circumference of the balloon portion 111 is an inside layer 112 composed of an elastic material excellent in ultrasonic wave transmittance and the outside circumference thereof is a balloon layer 113 excellent in ultrasonic wave transmittance and covering the outside circumference of the inside layer 112.

The endoscope cover 110 is integrally provided with a balloon water feed tube 114, an end thereof has an opening on the outside circumference of the inside layer 112, and the other end thereof is connected to a deaerated water feed port disposed in the vicinity of an operating unit side (not shown).

In the endoscope cover type endoscope arranged as described above, deaerated water is fed from the deaerated water feed port in the state that the endoscope cover 110 is mounted to the ultrasonic covering type endoscope 61. Thus, the deaerated water is fed between the inside layer 112 and the balloon layer 113 through the balloon water feed tube 114. The balloon portion 111 is expanded by the pressure under which the deaerated water is fed. More specifically, the balloon layer 113 is expanded to the outside circumference side and further the inside layer 112 tries to expand to the inside circumference because it is also the elastic member. With this arrangement, the inside layer 112 is pressed against the outside circumference of the contained unit 71 of the ultrasonic covering type endoscope 61 and comes into intimate contact therewith, and thus the air layer between the ultrasonic covering type endoscope 61 and the endoscope cover 110 is removed.

When the balloon layer 113 is expanded greater than the diameter of the lumen in a human body, the outside circumference of the balloon layer 113 comes into intimate contact with the lumen wall in the human body by feeding deaerated water. With this arrangement, the air layer by which an ultrasonic wave from the ultrasonic covering type endoscope 61 is attenuated can be entirely removed without filling the lumen with the deaerated water, and thus an excellent ultrasonic image can be obtained. In this case, since the extreme end of the endoscope cover type endoscope is fixed in the lumen, a usual optical observation can be easily effected.

Note, when the balloon layer 113 is not sufficiently expanded, it suffices to effect a test by using the deaerated water feed method in combination. Further, the deaerated water may be fed by using any method and, for example, a method of using an endoscope cover expansion unit or, a method of using a roller pump, may be used.

Figure 15:
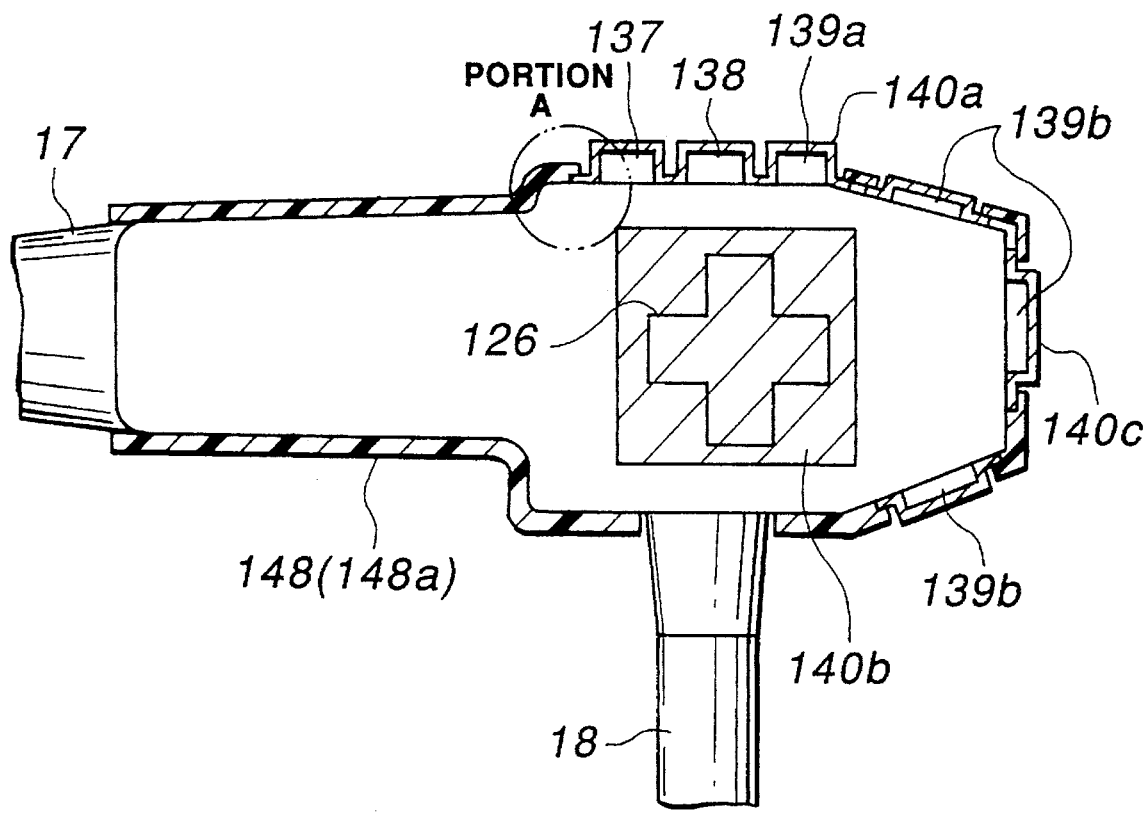
Figure 16:
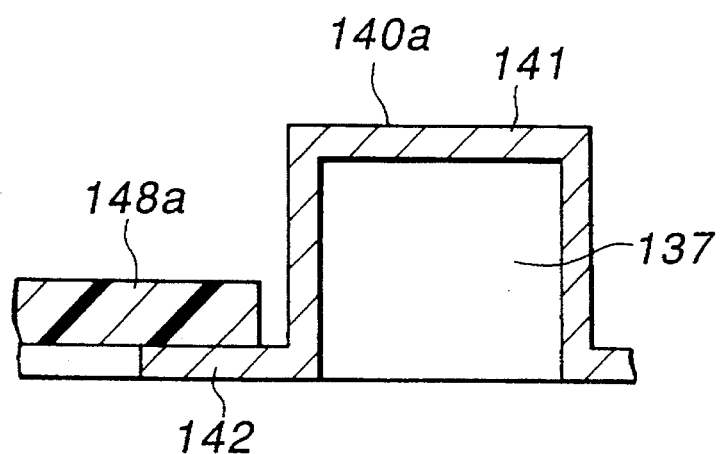
Figure 17:
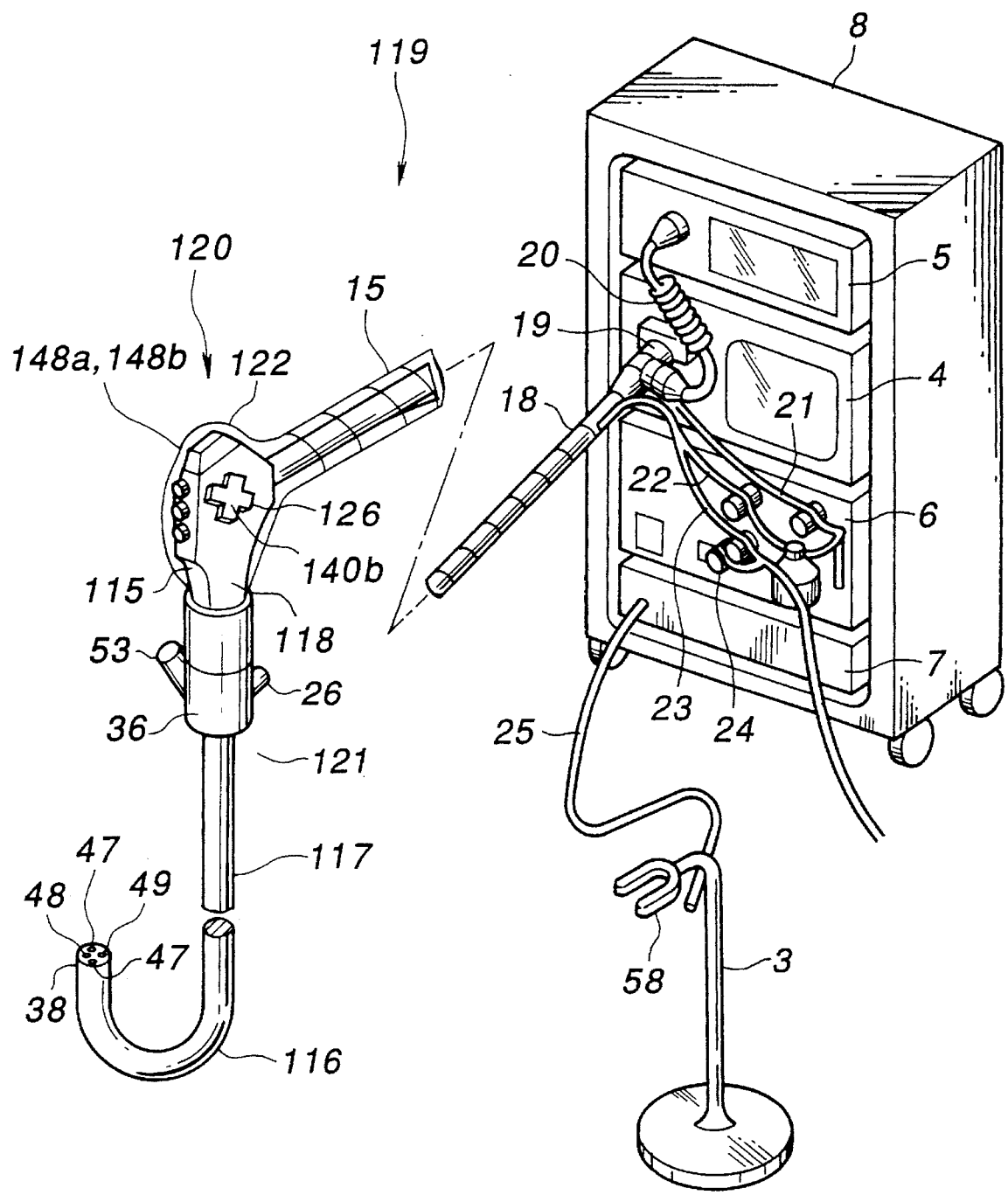
Figure 18:
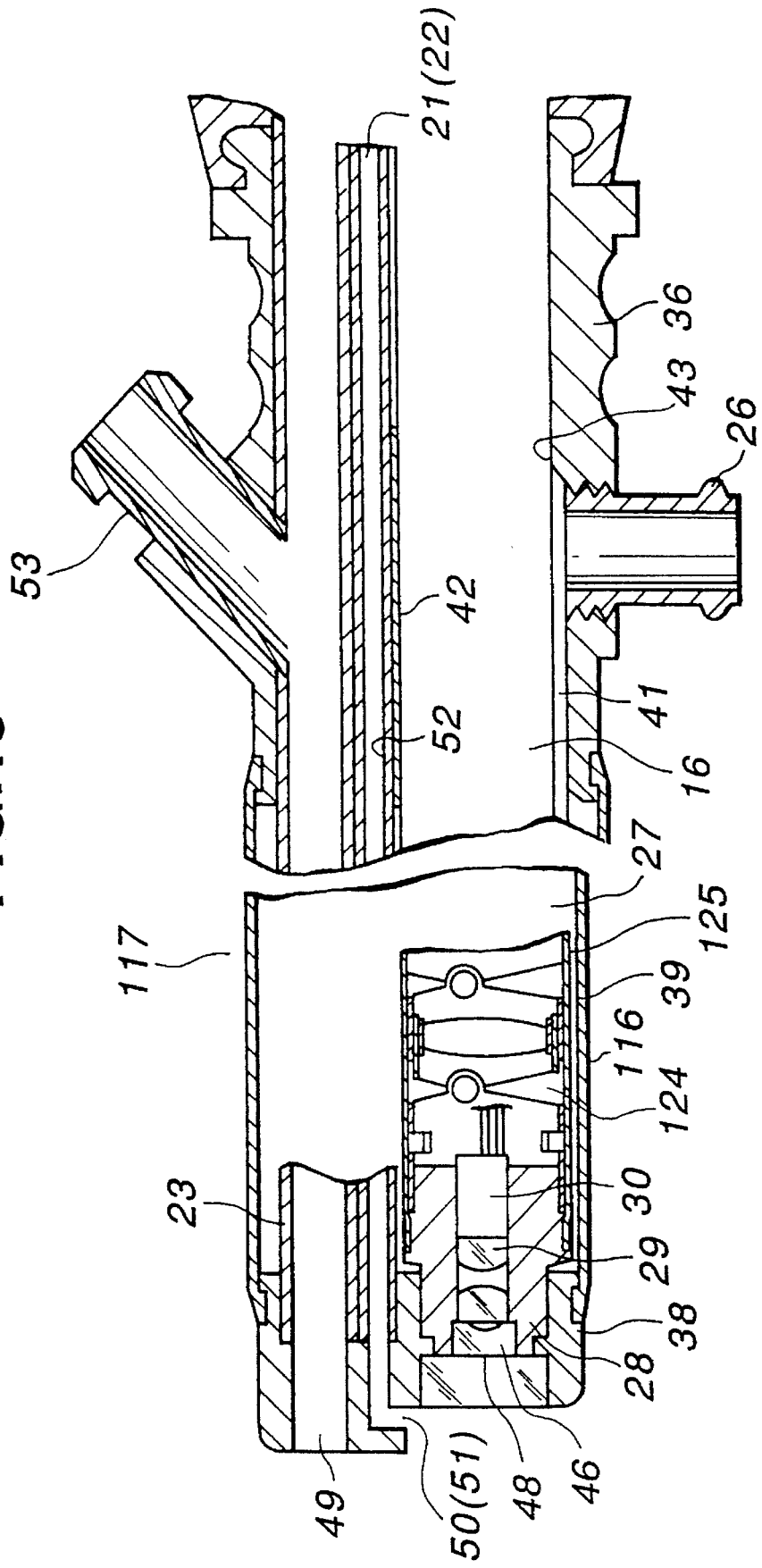
Figure 19:
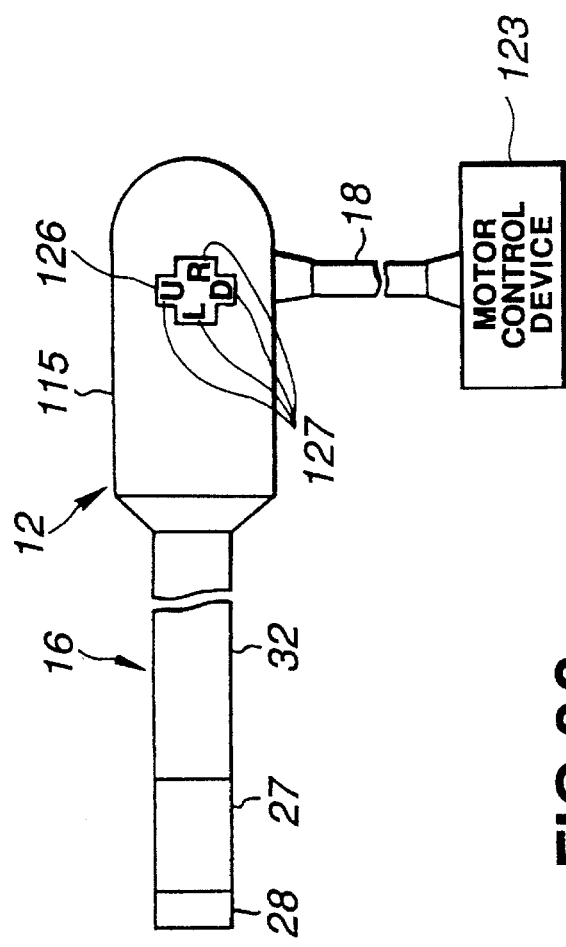
Figure 20:
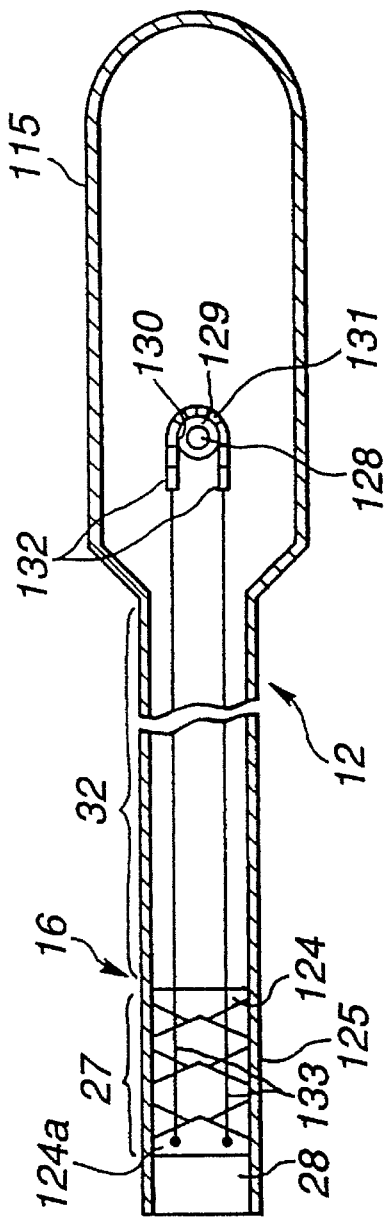
Figure 21:
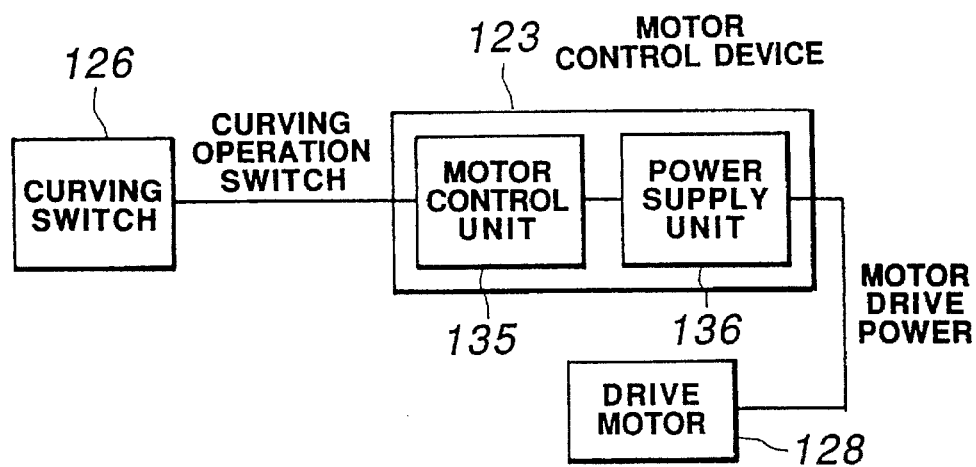
Figure 22:
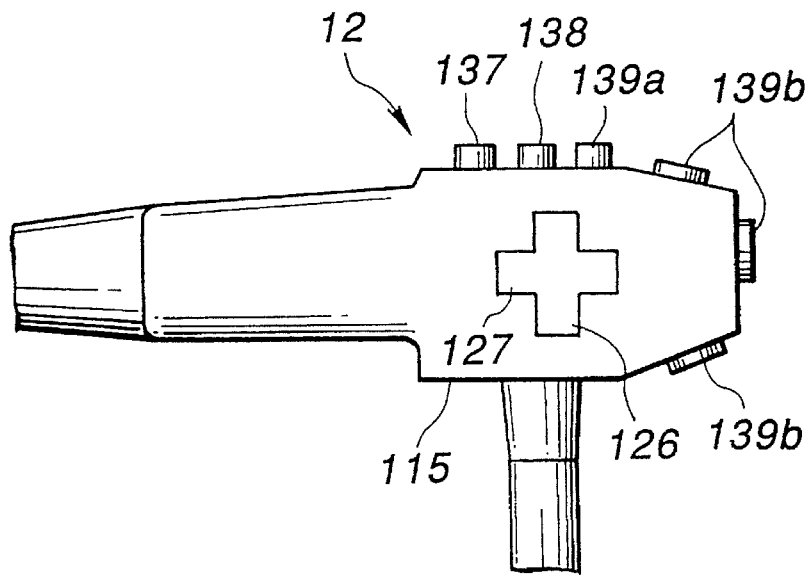
Figure 23:
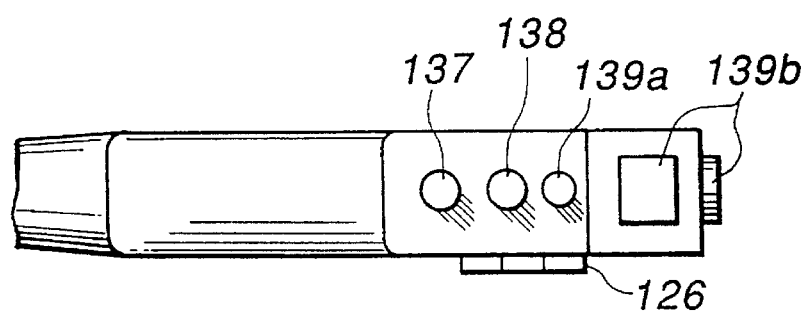

FIG. 15 to FIGS. 28(A) and 28(b) relate to a sixth embodiment according to the present invention, wherein: FIG. 15 is an explanatory diagram showing the vicinity of the operating unit of an endoscope cover type endoscope with a channel; FIG. 16 is an enlarged diagram showing the portion A in FIG. 15 in enlargement; FIG. 17 is an overall perspective view of an endoscope apparatus using an endoscope cover type endoscope with a channel; FIG. 18 is a side cross sectional view showing the state that the inserting portion cover of an endoscope cover with a channel is mounted to the inserting portion of a covering type endoscope; FIG. 19 is an explanatory diagram showing a covering type endoscope; FIG. 20 is an explanatory diagram showing the electrically operated curving unit of a covering type endoscope; FIG. 21 is a circuit block diagram enabling a curving drive; FIG. 22 is a side view showing the various switches disposed on an inserting unit; FIG. 23 is a front view of FIG. 22; FIGS. 24(A) and 24(b) to FIGS. 26(A) and 26(b) are explanatory diagrams showing a switch cover; and FIGS. 27(A) and 27(b) and 28(A) and 28(b) are explanatory diagrams showing a hard cover.

First, the endoscope apparatus as a whole will be described with reference to FIG. 17.

The endoscope apparatus 119 shown in FIG. 17 is composed of an endoscope cover type endoscope with a channel 120, cover holder 3, light source 4 as a peripheral unit, video processor 5, fluid control unit 6, endoscope cover expansion unit 7, and a cart 8 in which these peripheral units are accommodated. The endoscope cover type endoscope with a channel 120 is composed of a combination of an endoscope cover with a channel 121 and covering type endoscope 118 and when a test is performed, the covering type endoscope 118 is covered with the endoscope cover with a channel 121. The endoscope cover with a channel 121, which covers the inserting portion 16 and the like of the covering type endoscope 118 so that the endoscope need not be rinsed and sterilized after the test has been completed, is composed of an inserting portion cover 117, operating unit cover 122, and universal cord cover 15.

As shown in FIG. 19, the covering type endoscope 118 includes an operating unit 115 and a slender inserting portion 16 connected to the operating unit 115 and capable of being inserted into a testing member from a hand side. The inserting portion 16 of the covering type endoscope 118 includes a soft portion 32, curving portion 27 capable of being curved and hard extreme end 28 from the hand side of the operating unit to the extreme end thereof. Note, the inserting portion 16 has a cross-section formed to, for example, a semicircular shape to secure a space for the tubes 21 to 23 of the endoscope cover with a channel 121. FIG. 18 shows the state that the inserting portion 16 of the covering type endoscope 118 is covered with the endoscope cover with a channel 121.

As shown in FIG. 18, an illuminating optical system (not shown) and observing optical system 29 are disposed at the extreme end 28 of the inserting portion 16. Then, the emitting end of a not shown light fiber guide (not shown) is disposed at the rear end of the illuminating optical system, and an illuminating light supplied from the light source 4 by the light guide fiber passing through the inserting portion 16, operating unit 115 and universal cord 18 illuminates the interior of the lumen. A solid photographing device 30 is disposed at the rear end of the observing optical system 29 to convert a light reflected from an observing portion to an electric signal. The electric signal from the solid photographing device 30 is supplied to the video processor 5 through the aforesaid signal cord 20.

On the other hand, the inserting portion cover 117 of the endoscope cover with a channel 121 is used to cover the inserting portion 16 of the covering type endoscope 118, the operating unit cover 122 is used to cover the operating unit 115 of the covering type endoscope, and the universal cord cover 15 is used to cover the universal cord 18. Then, the covering type endoscope 118 is used for a test in a state in which all the covers 13, 122 and 15 are mounted.

The inserting portion cover 117 is formed to have a slender shape and is composed of an endoscope operating unit fixing mouth member 36, flexible cover portion 116 and cover extreme end portion 38 disposed from the hand side, as shown in FIG. 18. The endoscope operating unit fixing mouth member 36 and cover extreme end portion 38 are composed of a hard material. Further, the flexible cover portion 116 between the endoscope operating unit fixing mouth member 36 and the cover extreme end portion 38 is flexible and the surface thereof is covered with an inserting portion cover casing 39. As shown in FIG. 18, the arrangement of the inserting portion cover 117 is the same as that of the inserting portion cover 13 shown in FIG. 1.

In this embodiment, the curving portion 27 of the inserting portion 16 is electrically curved. As shown in FIG. 19, the universal cord 18 is connected to the side of the operating unit 115 of the electrically curving covering type endoscope 118 and also to a motor control unit 123 in addition to the light source 4 of FIG. 17. Further, a curving switch 126 is disposed on the operating unit 115 to indicate a curving direction of the curving portion 27. The curving switch 126 includes curving direction indicating units 127 to curve the curving portion 27 of the inserting portion 16 in the upward, downward, left and right directions.

As shown in FIG. 20, the operating unit 115 includes a DC drive motor 128 for curving the curving portion 27 in the upward and downward directions, sprocket 130 fixed to the drive shaft 129 of the drive motor 128, and a curving chain 131 meshed with the sprocket 130. Then, curving operation wires 133, 133 are connected to the ends of the curving chain 131 through curving connection members 132, 132.

On the other hand, as shown in FIGS. 18 and 20, the curving portion 27 of the inserting portion 16 includes a curving tube 125 to which a plurality of curving pieces 124 are connected in the interior thereof. The curving operation wires 133, 133 pass through the soft portion 32 and curving portion 27 and are connected to the curving piece 124a at the most extreme end.

The drive of the curving portion 27 arranged as described above is controlled by the curving switch 126. More specifically, when the curving direction indicating units 127 for the respective directions of the curving switch 126 are selectively depressed, a curving operation signal in accordance with a selected and indicated direction is produced. As shown in FIG. 21, the curving operation signal is input to the motor control unit 135 provided in the motor control unit 123 through the not shown cable in the universal cord 18. The motor control unit 135 detects a curving direction designated by the input curving operation signal, determines a motor to be driven and its rotating direction and indicates to supply of an electric power to a power source 136. When a drive, for example, in the upward/downward direction is designated by the curving direction instructing unit 127, the drive motor 128 is supplied with the driving power from the power source 136 through cable a (not shown) in the universal cord 18 so that the drive motor 128 is driven in the designated direction.

The rotation of the drive motor 128 is transmitted to the curving portion wires 133 through the drive shaft 129, sprocket 130 and curving chain 131. Thus, the upper and lower curving operation wires 133, 133 are pulled or loosened so that the curving piece 124a at the extreme end is moved upward or downward to curve the curving portion 27.

Note, although FIG. 20 relates to a device for curving the curving portion 27 upward and downward, a device for curving the same to the right and left directions has a similar arrangement and thus it is not shown and described here.

The operating unit 115 of the covering type endoscope 118 includes various switches in addition to the curving switch 126. FIG. 22 shows the side view of the operating unit 115 of the electrically curving type covering type endoscope 118 and FIG. 23 show the upper surface thereof.

As shown in FIGS. 22 and 23, the curving switch 126 is disposed on the side of the operating unit 115, an air/water feed switch 137 for feeding air and water and suction switch 138 for effecting suction are disposed on the upper surface thereof, and function switches 139a, 139b are disposed for photographing on the rear surface thereof. The curving switch 126 is a cross-shaped pad switch having four projections in correspondence with the upward, downward, right and left directions toward which the curving portion 27 is curved, and each projection constitutes the curving direction instructing unit 127. A curving direction of the curving portion 27 is instructed by forcibly inserting each curving direction instructing unit 127 to the side of the operating unit 115. The air/water feed switch 137 and suction switch 138 are formed to have a column shape and the feed of air/water or suction is instructed by forcibly inserting them to the side of operating unit 115. Further, the function switches 139a, 139b are formed to a column shape or square pillar shape and various functions are instructed by forcibly inserting them to the side the operating unit 115.

In this embodiment, the operating unit cover 122 for covering the operating unit 115 is composed of switch covers 140a to 140c for covering the respective switches and hard cover 148 for covering the portion of the operating unit 115 other than the respective switches.

FIGS. 24(A) and 24(b) show the switch cover 140a for covering the air/water feed switch 137 disposed on the operating unit 115, suction switch 138 and one of the function switches, 139a. The switch cover 140a is composed of a soft and sticky material and includes a portion 141 having shapes substantially similar to those of the air/water feed switch 137, suction switch 138 and one of the function switches, 139a and a film-like portion 142 around the portion 141.

FIGS. 25(A) and 25(b) show the switch cover 140b for covering the curving switch 126. The switch cover 140b is composed of a soft and sticky material and includes a portion 143 having a shape substantially similar to that of the curving switch 126 and a film-like portion 144 around the portion 143.

FIGS. 26(A) and 26(b) show the switch cover 140c for covering the function switch 139c disposed on the rear side of the operating unit 115. The switch cover 140c is composed of a soft and sticky material and includes a portion 145 having shapes substantially similar to those of the function switches 139b and a film-like portion 146 around the portion 145.

On the other hand, the hard cover 148 is divided into two parts, i.e., hard covers 148a and 148b, which cover in combination the operating unit 115 from the opposite sides thereof.

FIGS. 27(A) and 27(b) show the side of the hard covers 148a, 148b and FIGS. 28(A) and 28(b) show the upper side thereof. The hard cover 148b has an inside surface formed to a shape substantially similar to one outside surface of the operating unit 115 on the curving switch 126 side, and the hard cover 148a has an inside surface formed to a shape substantially similar to the other outside surface of the operating unit 115. A pair of the hard covers 148a, 148b are mated to each other on the divided surfaces 149, 149 thereof having the same shape. A plurality of fixing projections 150 are disposed on the divided surface 149 of the hard cover 148a, and a plurality of fixing recesses 151 are disposed on the divided surface 149 of the hard cover 148b at the positions corresponding to those of the fixing projections 150. When these hard covers 148a, 148b are combined, these fixing projections 150 are engaged with these fixing recesses 151 for intimate contact.

A pair of the hard covers 148a, 148b include suitable switch openings 152 (the hatched portion) disposed at the positions corresponding to the respective switches 126, 137, 138, 139a, 139b, these switch openings 152 having sizes and shapes corresponding to these switches. When only the hard covers 148a, 148b are mounted to the operating unit 115, these switch openings 152 enable the respective switches 126, 137, 138, 139a, 139b to be exposed without being covered with the hard cover 148. Further, the respective switch openings 152 are smaller than the film-like portions 142, 144, 146 of the switch covers 140a–140c located at the corresponding positions thereof, and thus when the inserting portion cover 122 is mounted, the respective switch openings 152 are closed by the film-like portions 142, 144, 146 of the respective switch covers.

Note, an opening 153 through which the universal cord 18 passes is also defined to the hard covers 148a, 148b.

In the endoscope cover type endoscope arranged as described above, first, the switch covers 140a–140c of the operating unit cover 122 are mounted to the operating unit 115, then the hard covers 148a, 148b are mounted. FIG. 15 shows the state that the switch covers 140a–140c and hard cover 148a are mounted to the operating unit 115; and FIG. 16 shows the portion A in enlargement.

More specifically, first, the switch cover 140b is mounted to the curving switch 126 of the operating unit 115, the switch cover 140a is mounted to the air/water feed switch 137, suction switch 138 and function switch 139a, the switch cover 140c is mounted to the respective switches 139b. With this arrangement, the respective switches 126, 137, 138, 139a, 139b are covered. The respective switch covers 140a to 140c have a sticking force, which prevents the respective switch covers 140a to 140c from being exfoliated from the surface of the operating unit 115.

Next, the hard covers 148a, 148b are mounted across the operating unit 115. In this case, the hard covers 148a, 148b are fixed by the engagement of the fixing projections 150 with the fixing recesses 151. The respective switches 126, 137, 138 139a, 139b covered with the switch covers 140a to 140c are exposed from the hard cover 148 through the respective switch openings 152 of the hard covers 148a, 148b. Moreover, since the sizes of the film-like portions 142, 144, 146 of the switch covers 140a to 140c are larger than those of the respective corresponding switch openings 152, the film-like portions 142, 144, 146 are held between the hard covers 148a, 148b and the operating unit 115, as shown in FIG. 16. With this arrangement, the operating unit 115 is covered with the operating unit cover 122 even at the vicinity of the respective switches.

As described above, in this embodiment, since the operating unit 115 is covered with the hard cover 122 divided to the two parts, a mounting job is very simple. Further, since the respective switches are covered with the soft switch covers 140a to 140c, the operation of the switches is not disturbed by these covers.

Note, the switch openings 152 of the hard cover 148 are not limited to the shape of the aforesaid example. Further, the position where the operating unit cover 148 is divided to the two parts is not limited to the substantially central position as in the aforesaid example. Note, this arrangement is also applicable to an angle knob type operating unit serving as the curving switch. Since, however, the pad switch which is not rotated is used as the curving switch, the switch cover for covering this curving switch need not be rotatably arranged. Therefore, the structure of the switch cover can be simplified and further the operation of the switches is not disturbed thereby.

Note, although the hard cover is arranged independently of the soft switch covers in this embodiment, they may be integrally arranged. In this case, the thus integrally arranged cover can be easily mounted and the operability of the switches can be improved.

Figure 29:
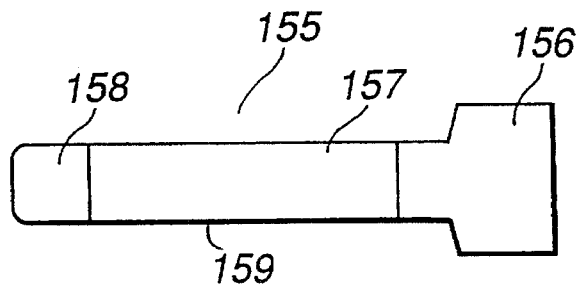
FIG. 29 is an explanatory diagram showing the inserting portion cover of an endoscope cover.
Figure 30:
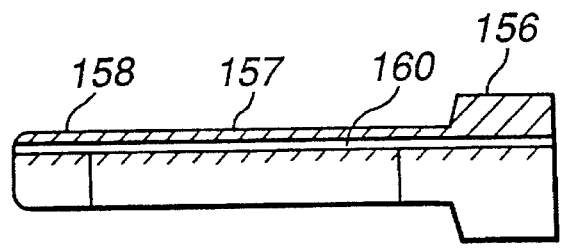
FIG. 30 is an explanatory diagram explaining an intestine gas removing tube in an inserting portion cover.
Figure 31:
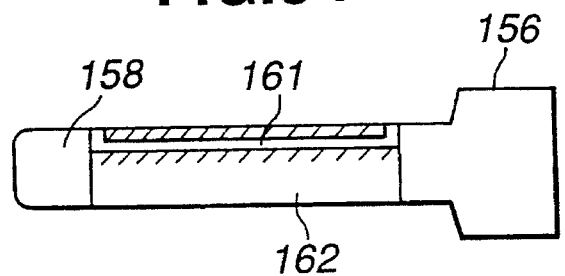
FIG. 31 is an explanatory diagram showing another example of the intestine gas removing tube.
Figure 32:
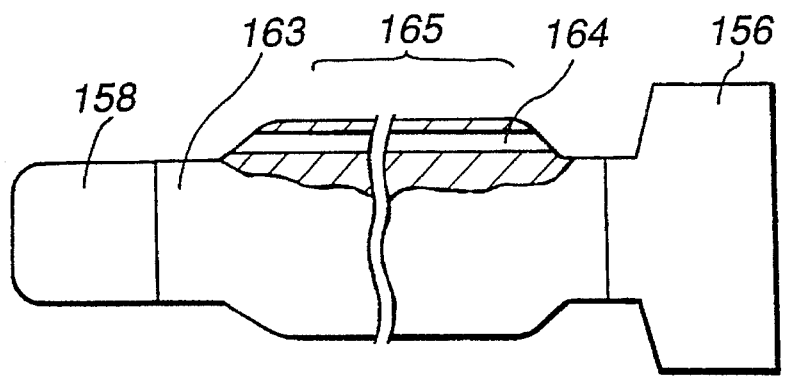
FIG. 32 is an explanatory diagram showing another example of the intestine gas removing tube.

FIGS. 29 to 32 relate to a seventh embodiment according to the present invention, wherein FIG. 29 is an explanatory diagram showing the inserting portion cover of an endoscope cover; FIG. 30 is an explanatory diagram explaining an intestine gas removing tube in an inserting portion cover; FIG. 31 is an explanatory diagram showing another example of the tube for removing a gas from an intestine; and FIG. 32 is an explanatory diagram showing another example of the intestine gas removing tube. This embodiment is applied to the removal of a gas in an intestine.

FIG. 29 shows an inserting portion cover 155 for covering the inserting portion 16 of a covering type endoscope 118. The inserting portion cover 155 is composed of an endoscope operating unit fixing mouth member 156, flexible cover portion 157 and cover extreme end portion 158. The flexible cover portion 157 has a surface composed of a flexible inserting portion cover casing 159.

As shown in FIG. 30, the inserting portion cover 155 includes an intestine gas removing tube 160 which passes through the cover extreme end portion 158, flexible cover portion 157 and endoscope operating unit fixing mouth member 156 and has an end opened at the extreme end of the cover extreme end portion 158 and the other end opened at the rear end of the endoscope operating unit fixing mouth member 156.

The endoscope cover type endoscope arranged as described above is inserted into an intestine in the state that the inserting portion cover 155 is mounted to the inserting portion 16. That is, the cover extreme end portion 158 reaches the intestine and the endoscope operating unit fixing mouth member 156 remains outside a human body. Therefore, the inside of the intestine is communicated with the outside of the human body through the intestine gas removing tube 160. In this way, gas in the intestine is expelled to the outside of the human body through the intestine gas removing tube 160. That is, gas in an intestine can be removed without using a special tool such as a sliding tube.

Note, the openings of the intestine gas removing tube need not always be provided at the extreme end of the cover extreme end portion 158 and the rear end of the endoscope operating unit fixing mouth member 156. For example, as shown in FIG. 31, the openings of an intestine gas removing tube 161 may be provided at the extreme end and rear end of a flexible cover portion 162.

Even in this case, a gas in an intestine can be removed by locating the extreme end of the intestine gas removing tube 161 to the inside of the intestine and the rear end thereof to the outside of an human body. Note, this case has an advantage that the intestine gas removing tube need not be provided with the cover extreme end portion 158 and the endoscope operating unit fixing mouth member 156.

Further, as shown in FIG. 32, a flexible cover portion 163 including a different shape portion 165 may be used. The flexible cover portion 163 is formed with the different shape portion 165 which is arranged such that an inserting portion cover casing rises to accommodate an intestine gas removing tube 164 therein. The intestine gas removing tube 164 has openings at the opposite ends of the different shape portion 165, and gas in an intestine can be expelled by locating the opening at an extreme end in the intestine and the opening at the hand side to the outside of a human body.

Figure 33:
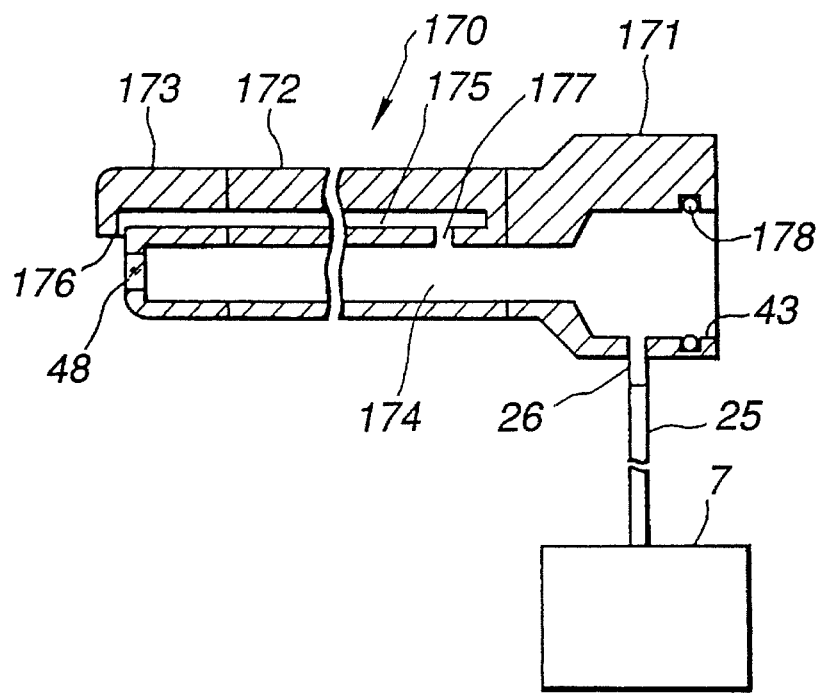
FIG. 33 is an explanatory diagram showing an example including the pump of an endoscope cover expansion unit and the pump of a fluid control unit as a shared pump.

FIGS. 33 and 34 relate to an eighth embodiment according to the present invention, wherein FIG. 33 is an explanatory diagram showing an example including the pump of an endoscope cover expansion unit and the pump of a fluid control unit as a shared pump; and FIG. 34 is an explanatory diagram showing another example including the pump of an endoscope cover expansion unit and the pump of a fluid control unit as a shared pump.

In FIGS. 1 and 17, there are provided the endoscope cover expansion unit 7 for expanding endoscope covers 11, 121 and fluid control unit 6. However, the pump in the endoscope cover expansion unit 7 may be shared with the pump in the fluid control unit 6. FIG. 33 shows an inserting portion cover enabling these pumps to be shared.

As shown in FIG. 33, an endoscope inserting channel 174 into which a covering type endoscope is inserted is provided with the endoscope operating unit fixing mouth member 171, flexible cover portion 172 and cover extreme end portion 173 of an inserting portion cover 170. Further, the inserting portion cover 170 includes an air feed tube 175 passing through the flexible cover portion 172 and cover extreme end portion 173, and the air feed tube 175 communicates with an air feed nozzle 176 opened toward an observing window 48 at the extreme end thereof. Further, the air feed tube 175 communicates with the endoscope inserting channel 174 and a communicating tube 177 in the flexible cover portion 172.

The endoscope inserting channel 174 communicates with the outside only through the communicating tube 177 and the opening 43 of the endoscope inserting channel 174 at the endoscope operating unit fixing mouth member 171. A watertight member 178 is provided on the inside circumference of the endoscope inserting channel 174 in the vicinity of the opening 43. The water tight member 178 is engaged with a watertight groove provided at the inserting portion of a covering type endoscope (not shown), and when the inserting portion of the covering type endoscope is inserted into the endoscope inserting channel 174, the inserting portion cover is kept in a water tight state by the engagement thereof. An expansion tube mouth member 26 is disposed on the side of the endoscope inserting channel 174 located nearer to the extreme end side than the water tight member 178 and projects to the outside of the endoscope operating unit fixing mouth member 171. An expansion tube 25 can be attached to the expansion tube mouth member 26. The expansion tube 25 feeds air fed from the endoscope cover expansion unit 7 to the endoscope inserting channel 174 through the expansion tube mouth member 26. Note, the endoscope cover expansion unit 7 can be controlled by turning ON/OFF the air/water feed switch disposed on the operating unit of the covering type endoscope.

In the endoscope cover type endoscope arranged as described above, the inserting portion is inserted into the endoscope inserting channel 174 and the expansion tube 25 is attached to the expansion tube mouth member 26. The opening 43 is closed by inserting the inserting portion and the endoscope inserting channel 174 is sealed by the watertight member 178.

The feed of air is instructed by the air/water feed switch in this state. This instruction is transmitted to the endoscope cover expansion unit 7 thorough the fluid control unit so that the operation of the pump (not shown) of the endoscope cover expansion unit 7 is started. With this arrangement, air from the endoscope cover expansion unit 7 is fed to the endoscope inserting channel 174 through the expansion tube 25 and expansion tube mouth member 26. The air is fed from the endoscope inserting channel 174 to the air feed tube 175 through the communicating tube 177 and further fed to the observing window 48 from the air feed nozzle 176. As described above, air is fed to the observing window 48 by making use of the pump of the endoscope cover expansion unit 7.

Figure 34A:
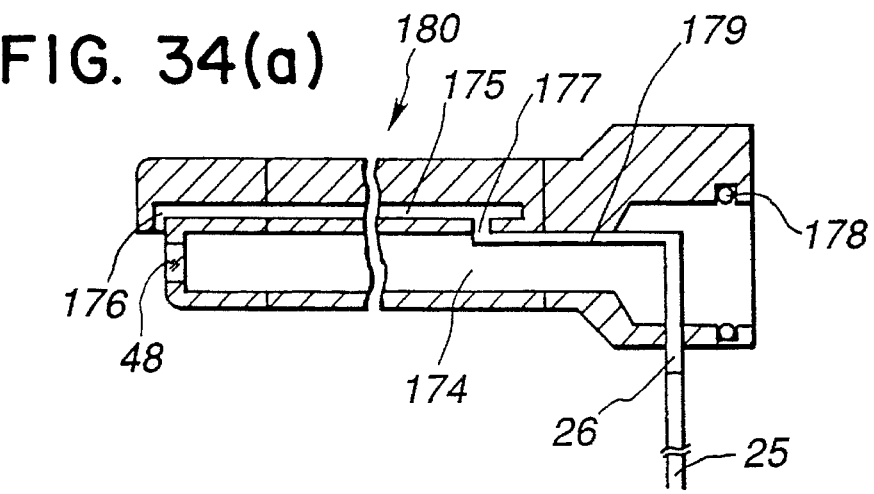
FIGS. 34(A) and 34(b) are explanatory diagrams showing another example including the pump of an endoscope cover expansion unit and the pump of a fluid control unit as a shared pump.
Figure 34B:
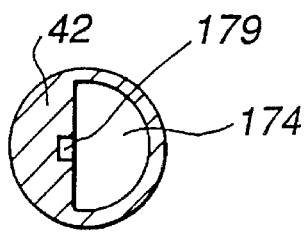

Further, FIGS. 34(A) and 34(b) show an example in which an amount of air fed to the observing window 48 is increased. FIG. 34(a) shows a side cross-sectional view of an inserting portion cover 180; and FIG. 34 (b) shows a cross-sectional of the inserting portion cover 180 at the position where a closing member 42 is cut off.

The endoscope inserting channel 174 has a semi-circular cross-sectional formed in accordance with the shape of the inserting portion. A recessed groove 179 having an end facing to the communicating tube 177 and the other end facing to the expansion tube mouth member 26 is formed to the closing member 42 on the circular arc side of the endoscope inserting channel 174.

According to this arrangement, air fed through the expansion tube mouth member 26 is fed to the air feed tube 175 through the gap defined between the endoscope inserting channel 174 and the inserting portion and the recessed groove 179 defined from the expansion tube mouth member 26 to the communicating tube 177. With this arrangement, since a sufficient space through which air is fed can be defined even in the state that the inserting portion is inserted into the endoscope inserting channel 174, a sufficient amount of air can be fed to the observing window 48.

Figure 35A:
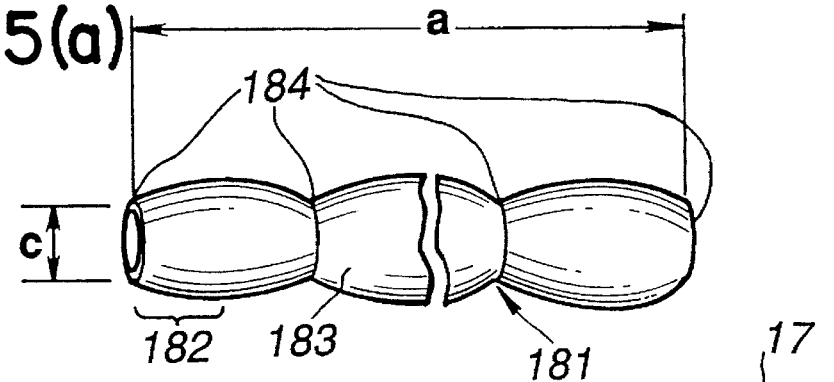
FIGS. 35(A) and 35(b) are explanatory diagrams showing a universal cord and a universal cord cover for covering a connector.
Figure 35B:
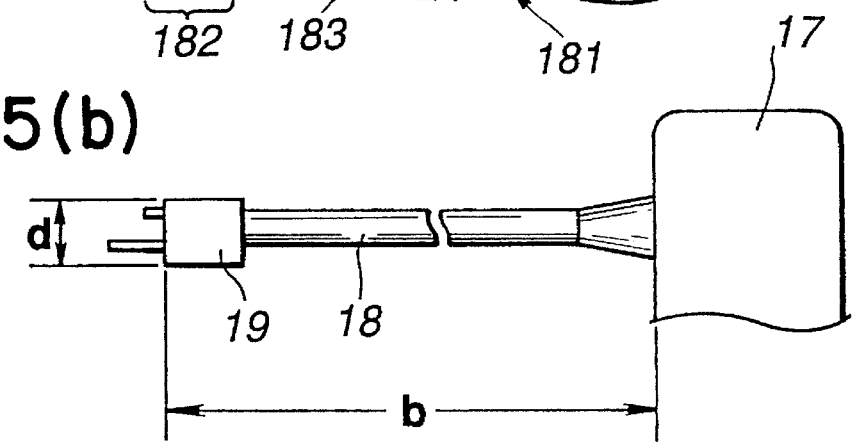
Figure 36A:
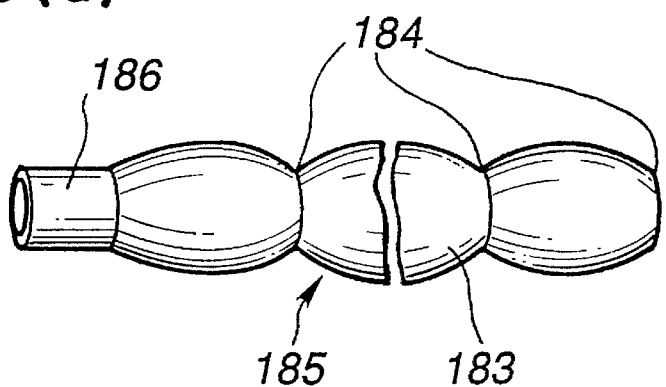
FIGS. 36(a) and 36(b) are explanatory diagrams showing another example of the universal cord cover.
Figure 36B:
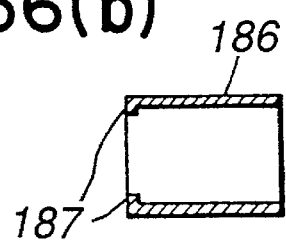

FIGS. 35(a), 35(b), 36(a) and 36(b) relate to a ninth embodiment according to the present invention, wherein FIGS. 35(A) and 35(b) are explanatory diagrams showing a universal cord and a universal cord cover for covering a connector; and FIGS. 36(A) and 36(b) are explanatory diagrams showing another example of the universal cord cover. This embodiment shows an example by which the universal cord cover can be easily mounted to the universal cord and connector.

FIG. 35(a) shows a universal cord cover 181; and FIG. 35(b) shows a universal cord 18 and connector 19. As shown in FIG. 35(b), a total length of the connector 19 and universal cord 18 is b. As shown in FIG. 35(a), the universal cord cover 181 is composed of a soft plastic tube-shaped member 183 and rubber bands 184 disposed at a plurality of positions of the tube-shaped member 183 including the ends thereof for pressing the tube-shaped member 183 toward the inside circumference thereof. Further, the universal cord cover 181 includes a connector accommodation unit 182 at the hand side thereof. A total length a of the universal cord cover 181 is set to a>b. Further, the tube-shaped member 183 has an inside diameter c larger than the outside diameter d of the connector 19 (c>d).

With this arrangement, since c>d, the universal cord cover 181 can be mounted from the connector 19 side having the diameter larger than that of the universal cord 18. Further, since the total length a of the universal cord cover 181 is longer than the length b of the connector 19 and universal cord 18, the connector 19 and universal cord 18 can be entirely covered with the universal cord cover 181. The connector 19 is covered with the connector accommodation unit 182, and the universal cord cover 181 is fixed to the universal cord 18 and connector 19 by the tightening force of the rubber bands 184.

Further, FIG. 36 shows an example in which the connector accommodation unit is composed of a hard member: wherein FIG. 36(a) shows a universal cord cover 185; and FIG. 36(b) shows a connector accommodation unit 186.

The universal cord cover 185 includes the hard connector accommodation unit 186 disposed at the hand side thereof. The connector accommodation unit 186 is integrally arranged with the tube-shaped member 183. The connector accommodation unit 186 includes a locking portion 187 defined at an end of the inside circumference thereof to position the connector 19 when it is mounted. In this case, the hard connector accommodation unit 186 having the locking portion 187 enables the connector 19 to be easily mounted, and thus the connector 19 and universal cord 18 can be easily covered.

Note, it is also possible that the soft tube-shaped member 183 is folded to the connector accommodation unit 182 or 186 side and the tube-shaped member 183 is extended to cover the universal cord 18 after the connector accommodation unit 182 or 186 has been mounted.

Figure 37A:
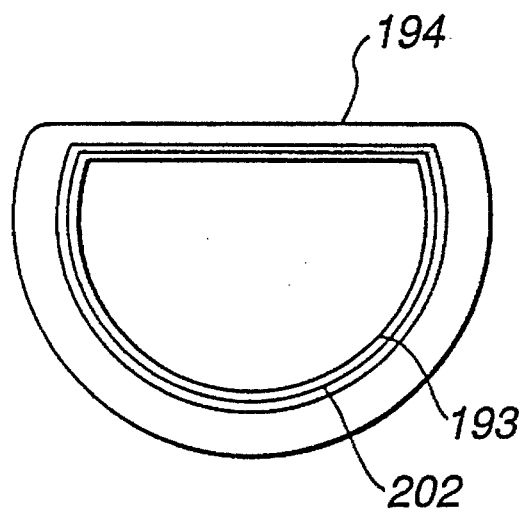
FIGS. 37(A) and 37(b) are explanatory diagrams showing the curving portion of a covering type endoscope.
Figure 37B:
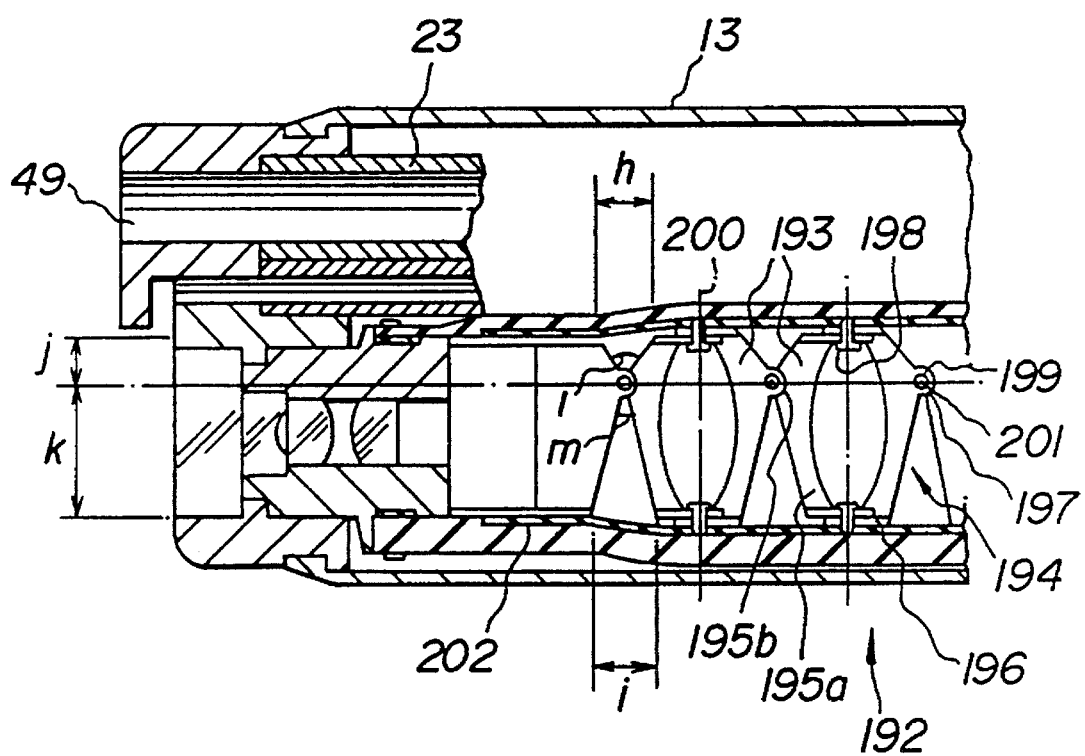
Figure 38:
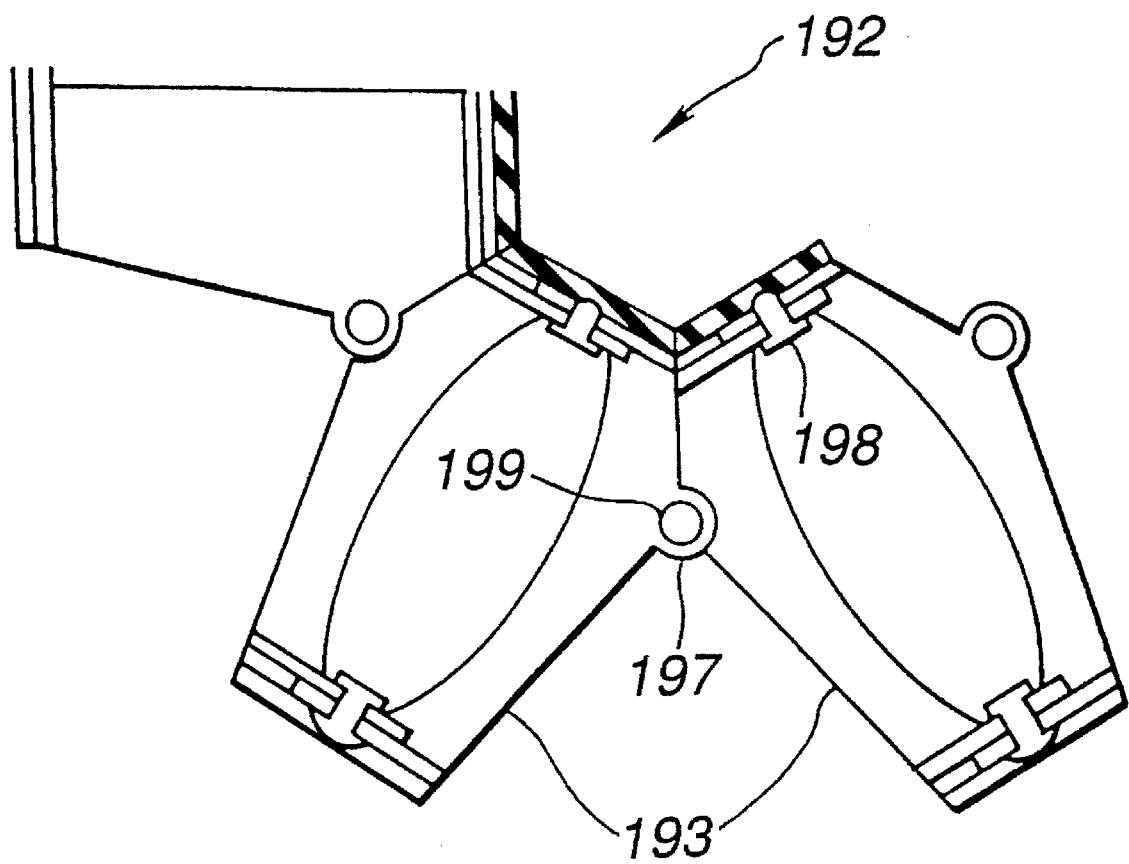
FIG. 38 is a diagram explaining the operation of the curving portion.

FIGS. 37 and 38 relate to a tenth embodiment according to the present invention: wherein FIG. 37 is an explanatory diagram showing the curving portion of a covering type endoscope; and FIG. 38 is a diagram explaining the operation of the curving portion.

This embodiment takes the curving of a covering type endoscope to which an endoscope cover is mounted into consideration. FIGS. 37(A) and 37(b) specifically show the arrangement of the curving portion 192 of the inserting portion of the covering type endoscope.

A plurality of curving pieces 193 are connected in the axial direction of the curving portion 192. The curving piece 193 is an annular member having a surface along the inside circumference of a curving tube 194 and has projections 195a, 195b in a connecting direction (front to back direction) which project in a reverse direction to each other on the upper surface and lower surfaces and the right and left central portions. More specifically, when viewed from the side (from the direction vertical to the paper), the curving piece 193 projects in one direction at the projections 195a on the upper and lower surfaces and in the reverse direction at the projections 195b at the central positions. Further, when viewed from the upper surface thereof, the curving piece 193 projects in one direction at the projection 195a at the central position and in the reverse direction at the projections 195B on the right and left surfaces. The curving piece 193 includes a pair of connecting pieces 196 formed to the projections 195a on the upper and lower surfaces and a pair of connecting pieces formed to the projections 195b at the central position. Then, in the adjacent pieces 193, the connecting pieces 196 or connecting pieces 197 are rotatably connected to each other by support shafts 198, 199, respectively.

More specifically, the adjacent curving pieces 193 can be rotated in the right and left directions by the vertical support shaft 198 and rotated upward and downward by the horizontal (right to left) support shaft 199. With this arrangement, the curving portion 192 is curved in the right and left directions about a rotating shaft 200 and in the vertical direction about a rotating shaft 201. Note, each of the curving pieces 193 is covered with a blade 202. Further, as shown in FIG. 37, the curving portion has a circular arc cross section and each connecting piece 197 is located at the center of the circular arc in the vertical direction.

A vertical curving angle is determined by the shoulder space between the curving pieces 193 connected by the connecting piece 197, i.e., the horizontal and vertical distances h, i, j, k of the portions between the upper and lower surfaces of the curving pieces 193 and the connecting pieces 197. More specifically, as the distances h, i of the horizontal shoulder space are larger, a maximum curving angle is increased, and as the distances j, k of the vertical shoulder space are smaller, a maximum curving angle is increased. In FIG. 37, although the distance h of the shoulder space on the upper surface side is substantially the same as the distance i of the shoulder space on the lower surface side, the distance j of the shoulder space on the upper surface side of the connecting piece 197 is set smaller than the distance k of the shoulder space on the lower surface, and thus the curving portion 192 is arranged such that the upper surface side is set to have a curving angle larger than that of the lower surface side. Further, when the curving portion 192 is not curved vertically, angles l, m formed by the connecting piece 197 and the upper and lower shoulder spaces of the adjacent curving pieces 193 are set to l>m.

Further, although the distance h of the shoulder space is set substantially equal to the distance i thereof, these distances h, i may be set to i>h by changing the shape of the curving pieces 193. Thus, for example, the curving portion 192 can obtain the same curving angle for both of the upper surface and lower surface thereof.

FIG. 38 shows a case in which the curving portion 192 is curved to its upper surface side with a maximum angle.

The curving pieces 193 are rotated about the support shaft 199 and the shoulder spaces of the curving pieces 193 on the upper surface side of the connecting piece 197 come into contact with each other, which the state the curving pieces are curved to its upper surface side by the maximum angle.

This embodiment is arranged such that the curving angle in each direction of the inserting portion 191 as a single body is set larger than the curving angle needed in the state that an inserting portion cover 9 is mounted to the inserting portion 191.

In the endoscope cover type endoscope arranged as described above, when it is assumed that a curving angle needed in each direction is, for example 180° in the state that an inserting portion cover 13 is mounted to the inserting portion 191, a curving angle in each direction obtained by the inserting portion 191 as a single body is set to 200°. It is assumed now that the curving portion 192 is curved in directions other than the direction toward the upper surface side (a contained unit side) in the state that the inserting portion cover 13 is mounted to the inserting portion 191. In this case, since the inserting portion 191 is not so affected by the contained unit, it can be curved by a curving angle of about 190°, whereas when the curving portion 192 is curved in the direction toward the contained unit, the curving angle of the inserting portion 191 is limited to 180° because it is greatly affected by the contained unit.

As described above, when the inserting portion cover 13 is mounted to the inserting portion 191, only a curving angle smaller than that set to the inserting portion 191 as a single body can be obtained. Since, however, a curving angle obtained by the curving portion 191 as a single body is set larger than an angle that needed when the inserting portion cover 13 is mounted to the curving portion 191, i.e., since the latter angle is set by taking the decrease of a curving angle caused by the mounting of the inserting portion cover 13 into consideration, the necessary curving angle 180° can be obtained.

Note, an amount of decrease of the curving angle caused by the mounting of the inserting portion cover 13 is experimentally determined.

Further, as described above, when the inserting portion cover 13 is mounted, the curving of the inserting portion 191 is greatly limited in the direction toward the contained unit. To cope with this problem, a curving angle of the inserting portion 191 in the upper surface direction may be set larger than the curving angle in other directions. For example, the curving portion 192 may be arranged such that the inserting portion 191 as a single body is curved in the direction toward the contained unit by 200° and in the other directions by 190°.

With this arrangement, when the inserting portion 191 is curved in a state in which the inserting portion cover 13 is mounted thereto, an curving angle of, for example, 180° can be obtained in the direction toward the contained unit as well as in the other directions because a curving resistance in the direction toward the contained unit is larger than that in other directions. Thus, in this case, the same curving angle can be obtained in any direction.

Further, when the contained unit has a very large curving resistance, a maximum curving angle of the curving portion 192 in the upper surface direction may be set more larger than that in the lower surface direction. More specifically, the shape of the curving piece 193 is changed so that the horizontal distance h of the shoulder space on the upper surface side is set larger than the distance i thereof on the lower surface side. Further, a maximum curving angle in the upper surface direction is set larger than that in the horizontal direction, taking the horizontal direction also into consideration.

With this arrangement, a curving angle limited in the contained unit direction can be increased and thus a desired curving angle can be obtained in any direction.

Further, the reduction of a curving radius of the curving portion 192 can increase the limitation of a curving angle. It suffices to increase the angles l, m formed by the shoulder space made by the connecting piece 197 and the adjacent curving pieces 193, to reduce the curving radius. Further, the limitation of the curving angle in the horizontal direction can be increased by the same way.

FIGS. 39 to 42 relate to an eleventh embodiment according to the present invention and are explaining diagrams showing a method of assembling an inserting portion cover in accordance with the sequence of assembly steps.

An inserting portion cover 13 is composed of an endoscope operating unit fixing mouth member 36, flexible cover portion 37 with a surface covered with a flexible inserting portion cover casing 39, and cover extreme end portion 38 each disposed from the hand side, and air feed tube 21, water feed tube 22 and suction tube 23 passing therethrough. The inserting portion cover 13 can be obtained by assembling them.

Figure 39:
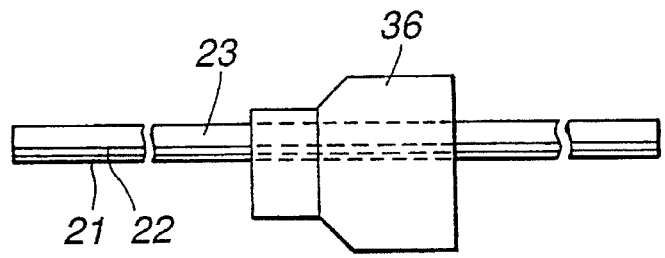
FIG. 39 to FIG. 42 are explaining diagrams showing a method of assembling an inserting portion cover in accordance with the sequence of assembly steps.

More specifically, at a first step shown in FIG. 39, the air feed tube 21, water feed tube 22 and suction tube 23 are caused to pass through the endoscope operating unit fixing mouth member 36 and fixed therein.

Figure 40:
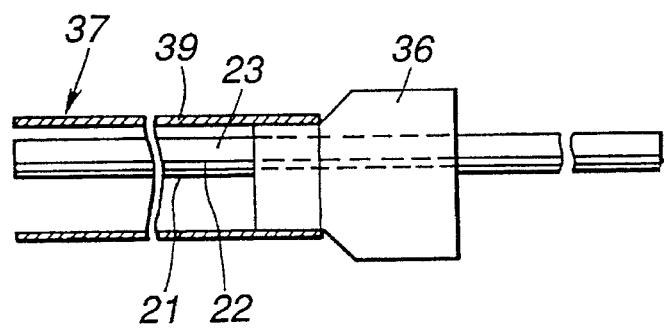

Next, at a second step shown in FIG. 40, the inserting portion cover casing 39 on the hand side of the inserting portion cover 13 is mounted to the inserting portion cover mounting surface provided at the extreme end of the endoscope operating unit fixing mouth member 36.

Figure 41:
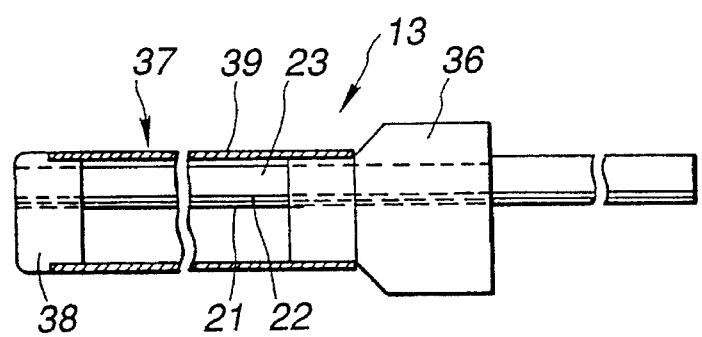

Finally, at a step 3 shown in FIG. 41, the hand side end of the cover extreme end portion 38 is connected to the extreme end of the inserting portion cover casing 39 as well as the air feed tube 21, water feed tube 22 and suction tube 23 in the flexible cover portion 37 are connected to the tubes 21, 22, 23 in the cover extreme end portion 38.

The assembly of the inserting portion cover 13 is completed by these three steps. When the inserting portion cover casing 39 is mounted to the endoscope operating unit fixing mouth member 36, the inside diameter of the inserting portion cover casing 39 need not be enlarged and a dedicated jig is not required. Moreover, when the inserting portion cover casing 39 is mounted, it need not be straightened, and thus a working space can be saved and an assembly job can be greatly simplified.

Note, although the air feed tube 21, water feed tube 22 and suction tube 23 passing through the inserting portion cover 13 are integrally extended up to a fluid control unit 6, tubes from the endoscope operating unit fixing mouth member 36 to the fluid control unit 6 may be separately arranged.

Figure 42:
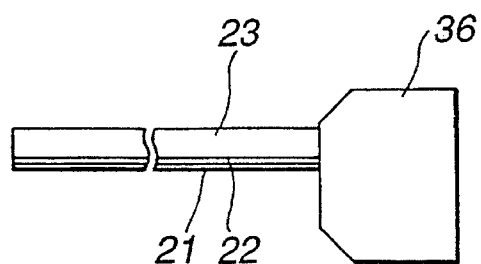

In this case, first, at a first step shown in FIG. 42, the air feed tube 21, water feed tube 22 and suction tube 23 are mounted to the endoscope operating unit fixing mouth member 36. Next, after the completion of the second and third steps shown in FIGS. 40 and 41, there is provided a fourth step at which the respective tubes from the fluid control unit 6 are connected to the tubes 21, 22 and 23 in the endoscope operating unit fixing mouth member 36.

In this arrangement, although one step is added, the setting of the tubes 21, 22 and 23 are made easy and thus an assembly job is simplified.

Figure 43:
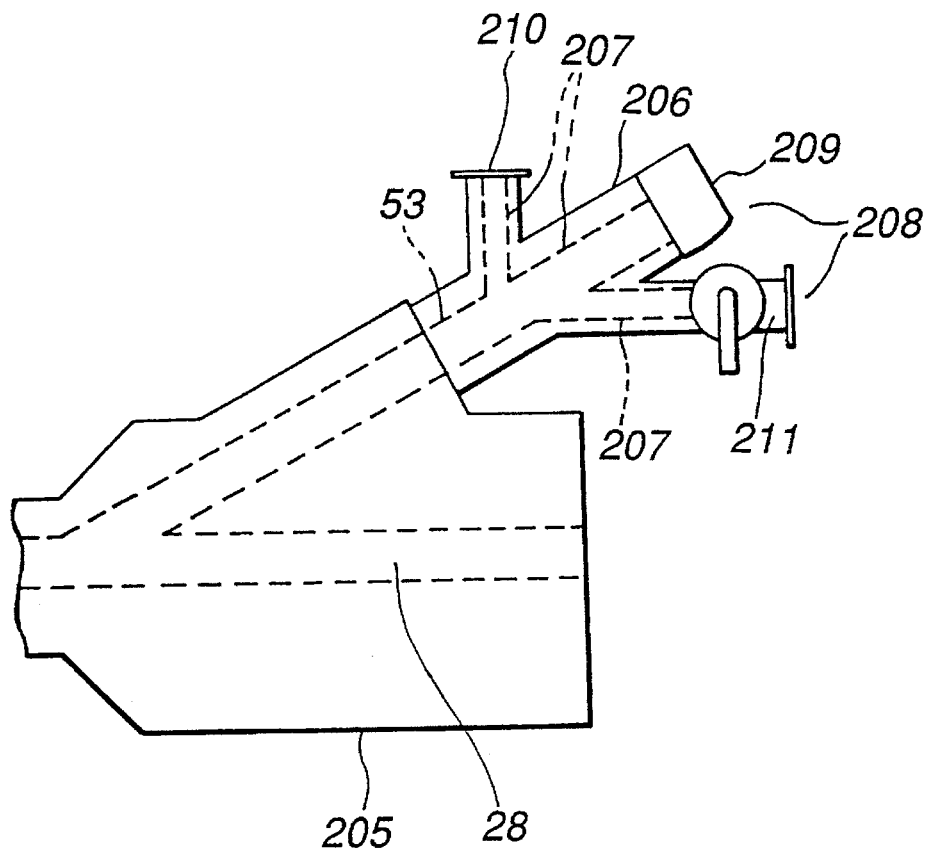
FIG. 43 is an explanatory diagram showing the vicinity of a forceps inserting port.
Figure 44:
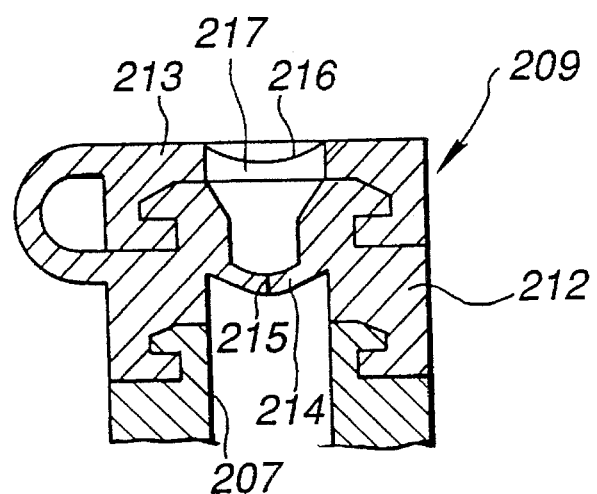
FIG. 44 is a cross sectional view showing a forceps stopper.

FIGS. 43 and 44 relate to a twelfth embodiment according to the present invention, wherein: FIG. 43 is an explanatory diagram showing the vicinity of a forceps inserting port; and FIG. 44 is a cross sectional view showing a forceps stopper. This embodiment shows an example in which accessories such as the forceps stopper are made disposable.

A suction tube 28 passes through an endoscope operating unit fixing mouth member 205 shown in FIG. 43 and the forceps inserting port 53 is communicated with the suction tube 28. A forceps inserting portion 206 having a branched extreme end is mounted to the end of the endoscope operating unit fixing mouth member 205 and the forceps inserting port 53 is branched to a plurality of branch tubes 207 in the forceps inserting portion 206 and faces to the outside. Various accessories 208 are mounted to the opening end of the branch tubes 207.

The accessories 208 include, for example, a forceps stopper 209, syringe mounting lure lock 210, two-way active stopper 211, and the like. Further, the accessories 208 also include a T-shaped tube, thruster, (not shown).

FIG. 44 shows the forceps stopper 209 in a specific form.

As shown in FIG. 44, the forceps stopper 209 is composed of a sealing stopper main body 212 and a cap 213 integrally formed with the main body 212 and detachably mounted on the upper portion of the main body 212. A first closing film 214 with a central portion projecting toward an inside path (projecting downward in the figure) is disposed on the upper portion in the sealing stopper main body 212 and a minus- or plus-shaped first slit 215 is defined at the center of the closing film 214. Further, a second closing film 216 is disposed on the upper surface of the cap 213 so that when the cap 213 is mounted to the sealing stopper main body 212, the second closing film 216 confronts the first closing film 214, and a second slit 217 is defined at the center of the closing film 216. The first and second slits 215, 217 are usually closed in an airtight state. Although the cap 213 may be removed, it is sometimes mounted to the sealing stopper main body 212 and an inserting tool (not shown) is inserted from the branch tube 207 to the forceps inserting port 53 through the first and second slits 215, 217. At this time, the first and second closing films 214, 216 come into intimate contact around the outside circumference of the inserting tool so that filthy things and air flowing backward in a path are prevented from leaking to the outside through the gap between the closing films 214, 216 and the inserting tool.

In the endoscope cover type endoscope arranged as described above, the various accessories 208 are sterilized in the state that they are mounted to the endoscope operating unit fixing mouth member 205 and an endoscope cover including the endoscope operating unit fixing mouth member 205 with the accessories 208 is provided to a user.

As a result, various accessories need not be replaced each time the endoscope cover type endoscope is used, and moreover, since the endoscope cover with the accessories is used in a sterilized state as a whole, there is no danger of contagion and thus safety is insured.

Figure 45:
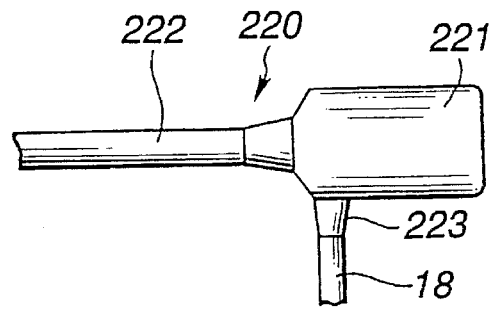
FIG. 45 is a side view showing a covering type endoscope.
Figure 46:
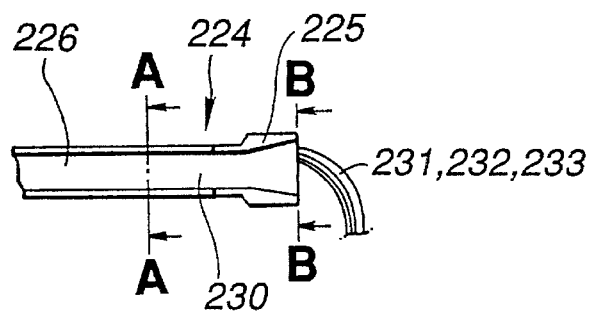
FIG. 46 is an explanatory diagram showing the cross section of an inserting portion cover.
Figure 47:
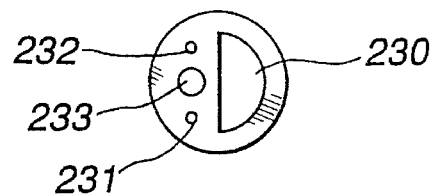
FIG. 47 is a explanatory diagram taken along the line A—A of FIG. 46.
Figure 48:
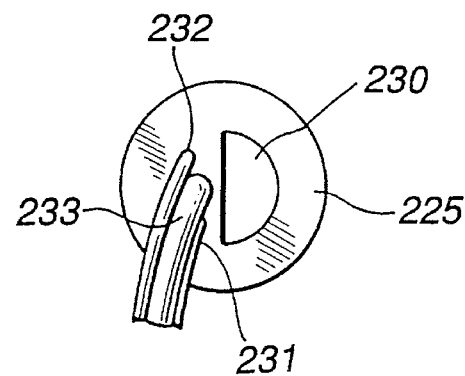
FIG. 48 is a diagram when
Figure 49:
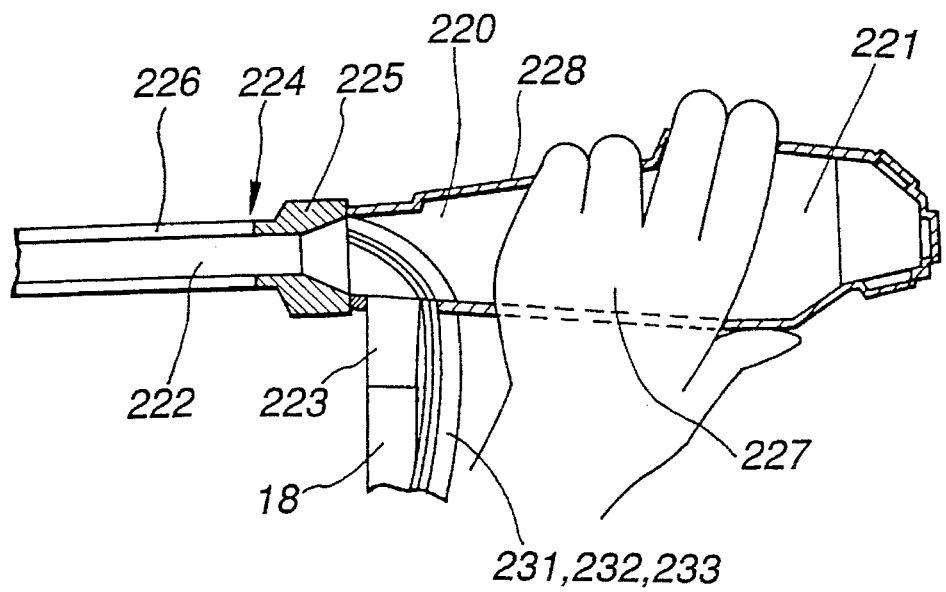
FIG. 49 is a side view showing the vicinity of the operating unit of an endoscope cover type endoscope shown in FIG. 45 to FIG. 48 in the state that the operating unit is gripped by a hand.

FIGS. 45 to 49 relate to a thirteen embodiment, wherein: FIG. 45 is a side view showing a covering type endoscope; FIG. 46 is an explanatory diagram showing the cross section of an inserting portion cover; FIG. 47 is a diagram taken along the line A—A of FIG. 46; FIG. 48 is a diagram when FIG. 46 is viewed from the line B—B thereof; and FIG. 49 is a side view showing the vicinity of the operating unit of an endoscope cover type endoscope shown in FIG. 45 to FIG. 48 in the state that the operating unit is gripped by hand.

An air/water feed tube and suction tube passing through an endoscope cover are extended up to a fluid control unit and the setting thereof must be taken into consideration. This embodiment shows an example by which the setting thereof is made easy.

In FIG. 45, an covering type endoscope 220 includes an operating unit 221 and inserting unit 222. A mounting portion 223 is disposed on the side of the operating unit 221 in the vicinity of the inserting portion 222. A universal cord 18 is connected through the mounting portion 223.

As shown in FIG. 46, an inserting portion cover 224 for covering the inserting portion 222 includes an endoscope operating unit fixing mouth member 225 at the hand side thereof and a flexible cover portion 226 at the extreme end thereof, and the operating unit 221 is mounted to the endoscope operating unit fixing mouth member 225. As shown in FIG. 47, an endoscope inserting channel 230 into which the inserting portion 222 is inserted, air feed tube 231, water feed tube 232 and suction tube 233 pass through the inserting portion cover 224, and as shown in FIG. 48, the tubes 231, 232, 233 are extended from the endoscope operating unit fixing mouth member 225 to the outside.

In the endoscope cover type endoscope arranged as described above, as shown in FIG. 49, the inserting portion cover 224 is mounted to the inserting portion 222 of the covering type endoscope 220 and an operating unit cover 228 is mounted to the operating unit 221. The operating unit 221 is gripped through the operating unit cover 228 to operate the various switches on the operating unit 221.

The mounting portion 223 to which the universal cord 18 is attached is disposed in the vicinity of the endoscope operating unit fixing mouth member 225 on the extreme side of the operating unit 221. More specifically, the position at which the tubes 231, 232, 233 are taken out from the endoscope operating unit fixing mouth member 225 is relatively near to the mounting portion 223. Therefore, the tubes 231, 232, 233 can be extended along the universal cord 18. Further, since the position of the mounting portion 223 is relatively spaced apart from the portion of the operating unit 221 gripped by a hand 227, the operation of the operating unit 221 is not prevented by these tubes 231, 232, 233 and universal cord 18.

As described above, since the position at which the tubes 231, 232, 233 are taken out is located near to the position where the mounting portion 233 is attached and further the mounting position is spaced apart from the position of the hand 227 in operation, the tubes 231, 232, 233 can be easily set and are excellent in workability.

Figure 50:
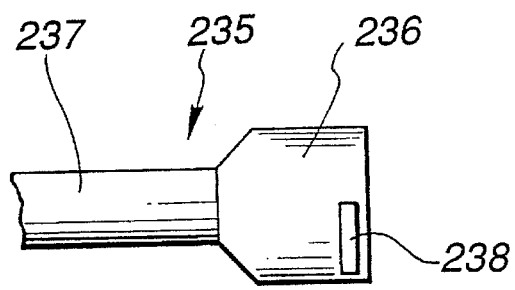
FIG. 50 is a side view showing the inserting portion cover of an endoscope cover.
Figure 51:
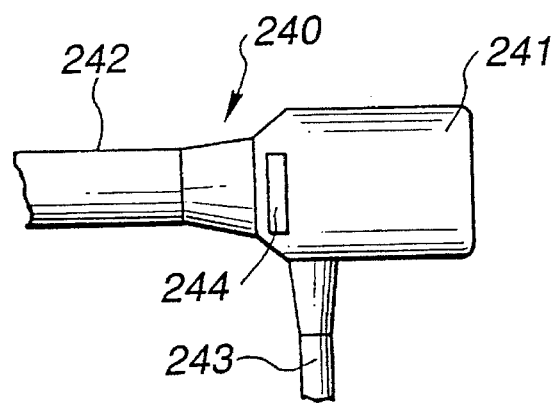
FIG. 51 is a side view showing a covering type endoscope.
Figure 52:
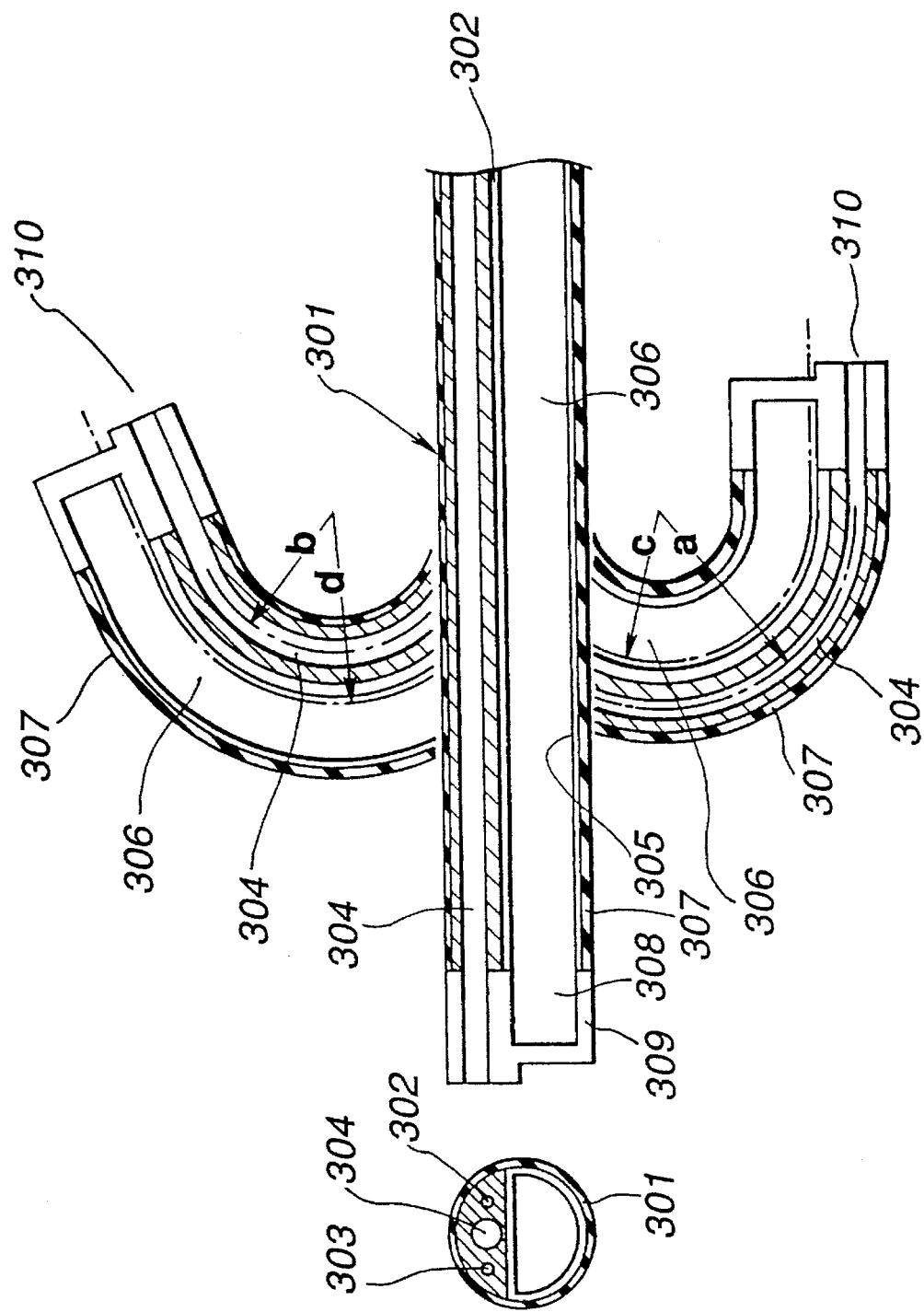
FIG. 52 is an explanatory diagram showing the state that the inserting portion of an endoscope is mounted to the inserting portion cover of an endoscope cover with a channel.
Figure 53:
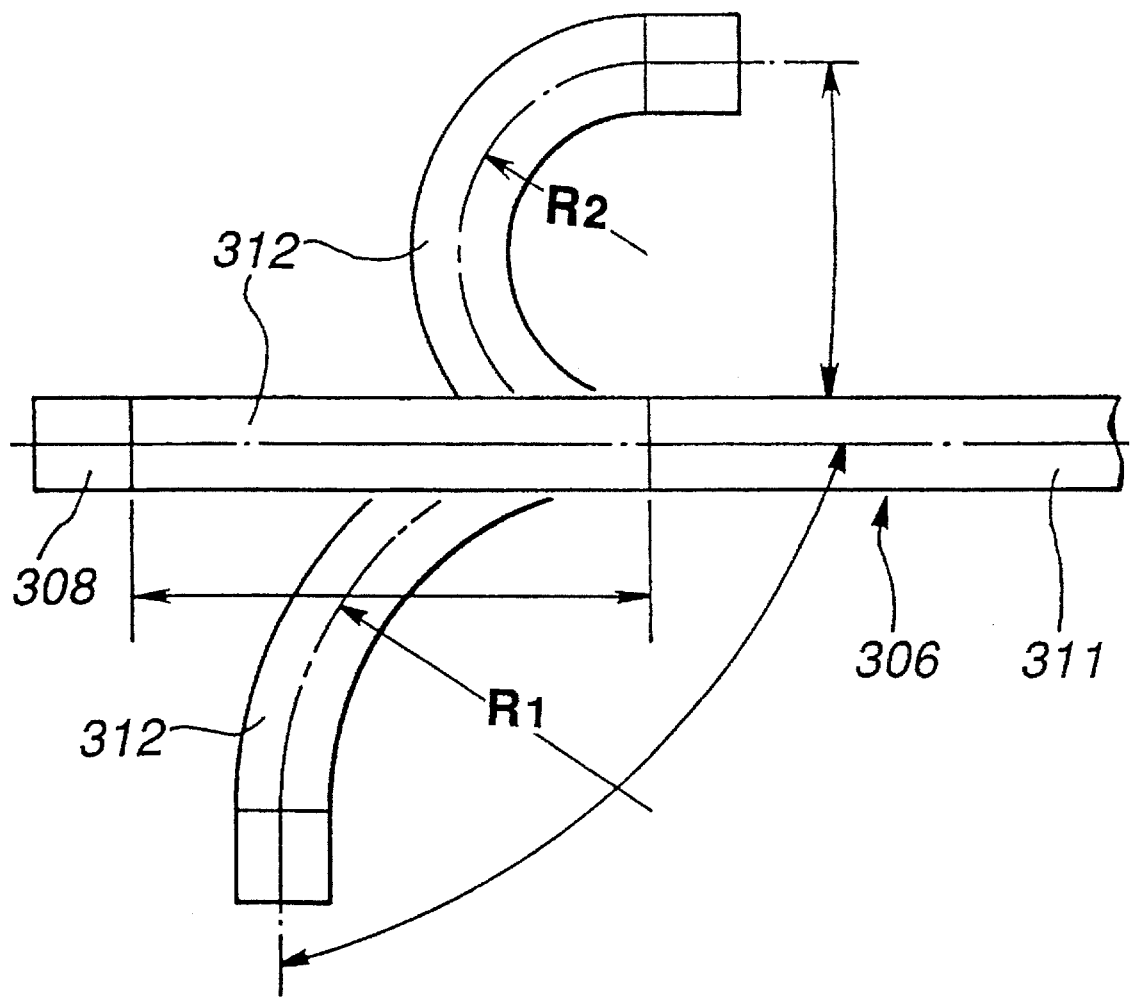
FIG. 53 is a diagram explaining a curving angle of an inserting portion to which an inserting portion cover is mounted.

FIGS. 50 and 51 relate to a fourteenth embodiment according to the present invention, wherein: FIG. 50 is a side view showing the inserting portion cover of an endoscope cover; and FIG. 51 is a side view showing a covering type endoscope. This embodiment shows an example by which an endoscope cover is mounted to a covering type endoscope by mistake.

In FIG. 50, the inserting portion cover 235 of an endoscope cover includes an endoscope operating unit fixing mouth member 236 at the hand thereof and a flexible cover portion 237 at the extreme end thereof. A name plate 238 on which the name of a covering type endoscope applicable to the inserting portion cover 235 is indicated is disposed on the surface of the endoscope operating unit fixing mouth member 236.

When the covering type endoscope is arranged as described above, a covering type endoscope applicable to the inserting portion cover 235 can be determined by confirming the name plate 238, and thus the mounting of the endoscope cover by mistake can be prevented.

Note, it is apparent that the name plate 238 need not be mounted at the position shown in FIG. 50.

Further, the combination of the inserting portion cover 235 and a covering type endoscope applicable thereto can be more easily determined by also indicating the name of the inserting portion cover 235 on the name plate 238.

In FIG. 51, a covering type endoscope 240 is composed of an operating unit 241 and inserting portion 242 and a universal cord 243 is connected to the operating unit 241. A name plate 244 on which the name of an inserting portion cover applicable to the covering type endoscope 240 is indicated is disposed on the surface of the operating unit 241.

The name of an inserting portion cover applicable to the covering type endoscope 240 is made apparent by confirming the name plate 244 and thus mounting by mistake can be prevented.

Note, it is apparent that the name plate 244 need not be mounted at the position shown in FIG. 51.

Further, the combination of the covering type endoscope 240 and an inserting portion cover applicable thereto can be more easily determined by also indicating the name of the covering type endoscope 240 on the name plate 244.

Further, the determination of an applicable covering type endoscope and inserting portion cover can be more easily determined by providing a name plate on which the names of the covering type endoscope and inserting portion cover are indicated with each of the covering type endoscope and inserting portion cover.

Further, marks of the same color may be provided with an applicable covering type endoscope and inserting portion cover in place of the provision of the name plate indicating their name. Color makes the determination of combination more easy.

Further, the same symbols may be attached to an applicable covering type endoscope and inserting portion cover. In this case, the combination of the applicable covering type endoscope and inserting portion cover can be determined by confirming the symbols.

Note, the name plate, the same color, same symbol and the like may be provided with packages for storing and transporting the inserting portion cover.

Further, the aforesaid is described only with respect to the inserting portion cover, it is apparent this is also applicable to an operating unit cover.

In the present invention, it is apparent that various embodiments may be made based on the present invention in a wide range without departing from the spirit and scope of the present invention. The present invention is not restricted by any specific embodiments thereof and only limited by the appended claims.

What is claimed is:

1. An endoscope cover type endoscope, comprising:

an endoscope having a curving portion composed of a plurality of curving pieces and an observation optical system; and an endoscope cover having an inserting path for inserting said endoscope and at least a fluid channel provided along said inserting path, wherein one side of each of said curving pieces facing said fluid channel is formed of a flat surface and a coupling portion coupling adjacent ones of said curving pieces is provided in a position displaced off a central axis of said endoscope near said flat surface of each of said curving pieces.

* * * * *